(12) United States Patent
Madjarov et al.

(10) Patent No.: US 9,993,339 B2
(45) Date of Patent: Jun. 12, 2018

(54) METHOD AND APPARATUS FOR THERAPY OF MITRAL VALVE

(71) Applicant: THE CHARLOTTE-MECKLENBURG HOSPITAL AUTHORITY, Charlotte, NC (US)

(72) Inventors: Jeko Metodiev Madjarov, Charlotte, NC (US); Sevtozar Madzharov, Sofia (BG); Charles Bridges, Charlotte, NC (US); Liam Ryan, Charlotte, NC (US)

(73) Assignee: THE CHARLOTTE-MECKLENBURG HOSPITAL AUTHORITY, Charlotte, NC (US)

( * ) Notice: Subject to any disclaimer, the term of this patent is extended or adjusted under 35 U.S.C. 154(b) by 0 days. days.

(21) Appl. No.: 14/774,832

(22) PCT Filed: Mar. 14, 2014

(86) PCT No.: PCT/US2014/028851
§ 371 (c)(1),
(2) Date: Sep. 11, 2015

(87) PCT Pub. No.: WO2014/144439
PCT Pub. Date: Sep. 18, 2014

(65) Prior Publication Data
US 2016/0030175 A1 Feb. 4, 2016

Related U.S. Application Data

(60) Provisional application No. 61/791,763, filed on Mar. 15, 2013.

(51) Int. Cl.
*A61F 2/24* (2006.01)

(52) U.S. Cl.
CPC .......... *A61F 2/2448* (2013.01); *A61F 2/2442* (2013.01); *A61F 2/2445* (2013.01);
(Continued)

(58) Field of Classification Search
CPC .... A61F 2/2442; A61F 2/2445; A61F 2/2448; A61F 2250/001; A61F 2250/0004; A61F 2250/0007
See application file for complete search history.

(56) References Cited

U.S. PATENT DOCUMENTS

| | | | |
|---|---|---|---|
| 2007/0142907 A1 | 6/2007 | Moaddeb | |
| 2009/0248148 A1* | 10/2009 | Shaolian | A61F 2/2448 623/2.37 |
| 2011/0202130 A1* | 8/2011 | Cartledge | A61F 2/2445 623/2.37 |

FOREIGN PATENT DOCUMENTS

| | | |
|---|---|---|
| WO | 2009120764 A2 | 10/2009 |
| WO | 2009126629 A1 | 10/2009 |

(Continued)

OTHER PUBLICATIONS

International Search Report for corresponding PCT Application No. PCT/US2014/028851, dated Jul. 28, 2014, 12 pages.

*Primary Examiner* — Dinah Baria
(74) *Attorney, Agent, or Firm* — John P. Zimmer; Nexsen Pruet, PLLC

(57) ABSTRACT

Devices and methods are described for treating a mitral valve defect. The device described includes features that allow the device to conform to the actual pathology of the valve, rather than attempting to replicate a healthy valve (which the patient does not have). In this way, the device allows the patient's actual value to work as well as possible, given the valve's diseased condition. The actual pathology of the valve is accommodated by providing for multiple dimensions of adjustability of the device, including adjust- (Continued)

ability of the size (e.g., diameter) of the device as well as adjustability of the elevation or inclination of one portion of the device (e.g., the portion supporting the posterior leaflet) with respect to another portion of the device.

12 Claims, 21 Drawing Sheets

(52) U.S. Cl.
CPC ......... *A61F 2220/0033* (2013.01); *A61F 2230/0008* (2013.01); *A61F 2230/0034* (2013.01); *A61F 2250/001* (2013.01); *A61F 2250/0007* (2013.01); *A61F 2250/0065* (2013.01)

(56) References Cited

FOREIGN PATENT DOCUMENTS

| | | |
|---|---|---|
| WO | 2010014671 A1 | 2/2010 |
| WO | 2012106344 A1 | 8/2012 |

\* cited by examiner

METHOD AND APPARATUS FOR THERAPY OF MITRAL VALVE

CROSS REFERENCE TO RELATED APPLICATIONS

This application is a U.S. national stage application under 35 U.S.C. § 371 of International Application No. PCT/US2014/028851 filed Mar. 14, 2014, which claims priority pursuant to 35 U.S.C. § 119(e) to U.S. Provisional Patent Application Ser. No. 61/791,763, filed Mar. 15, 2013, each of which is hereby incorporated by reference in its entirety.

FIELD OF THE INVENTION

The present invention relates generally to methods and apparatuses for treating the mitral valve of the heart. More specifically, methods and apparatuses are described for treating stenosis and/or regurgitation of the mitral valve.

BACKGROUND

The heart is an organ made up mostly of muscle tissue that is responsible for circulating oxygenated blood through an organism's blood vessels using regular, repeated contractions. To facilitate the flow of blood in one direction into the heart, through its various chambers, and out to the rest of the body, the mammalian heart has four valves: the tricuspid valve, the pulmonary valve, the mitral valve, and the aortic valve. In some cases, one of the valves may not function properly, such as due to a congenital defect or disease. The mitral valve, for example, which is responsible for allowing blood to flow from the left atrium of the heart to the left ventricle of the heart, in some cases may not fully open (known as stenosis). As a result, the amount of blood flowing through the heart is decreased, which can lead to serious complications such as atrial fibrillation, blood clots, and lung congestion, heart enlargement, and heart failure, among others. In other cases, the mitral valve may not fully close (known as regurgitation or leakage). In these cases, blood from the left ventricle may leak back into the left atrium, which may lead to problems such as atrial fibrillation, blood clots, infections, and heart failure, among others.

SUMMARY

Accordingly, a method and apparatus are provided for repairing a mitral valve in a way that may have improved safety, robustness, and simplicity for administering to a patient. A device for treating the mitral valve defect is provided that includes a frame comprising an adjustable member and a fixed member, where the frame defines a conformable shape of the device. Each connected end of the adjustable member may be engaged with a corresponding end of the fixed member, and a distance measured along the adjustment member from one connected end to the other connected end may be configured to be adjustable, such that a perimeter of the shape defined by the frame is adjustable. The device may be configured to be positioned proximate a base portion of a mitral valve and adjusted to conform to a shape of the mitral valve being treated so as to improve opening or closure of the mitral valve.

In some cases, each of the fixed member and the adjustable member may define a lumen, and the frame may further comprise a cinching member extending through the respective lumens of the fixed member and the adjustable member. The cinching member may be movable with respect to the fixed member and the adjustable member to adjust the perimeter of the shape. The adjustable member may comprise two free ends that are configured to be moved with respect to each other in response to a corresponding movement of the cinching member. For example, the cinching member may comprise two slotted ends disposed within the fixed member, and the device may further comprise an adjustment mechanism configured to be actuated by a user (e.g., the surgeon) to engage the slotted ends of the cinching member and move the slotted ends with respect to each other to adjust the length of the adjustable member. The adjustment mechanism may comprise a gear configured to be rotated solely in a first direction when the gear is in a first axial position and further configured to be rotated in a second direction when the gear is in a second axial position.

In some embodiments, the device may comprise an outer covering surrounding the frame. The outer covering may comprise at least one of a polymer material or polyester. The frame may comprise nitinol.

In some embodiments, the frame may comprise at least one hinge proximate adjoining ends of the adjustable member and the fixed member. The at least one hinge may be configured to allow adjustment of an elevation of the frame with respect to a reference plane passing through the fixed member. The at least one hinge may comprise a first hinge portion connected to an end of the fixed member and a second hinge portion connected to a corresponding end of the adjustable member, and the second hinge portion may be configured to be unlocked from the first hinge portion upon receipt of a pinching force applied by a user to the at least one hinge, thereby allowing adjustment of the elevation of the frame. The at least one hinge may be configured to allow adjustment of the elevation to an angle between approximately 0° and approximately 20°.

In some cases, the frame may comprise a predefined saddle shape. In still other cases, the frame may comprise a malleable material.

In other embodiments, a method for treating a mitral valve defect is provided that comprises providing a device having a frame comprising an adjustable member and a fixed member and placing the device proximate a base portion of a mitral valve to be treated. Each connected end of the adjustable member may be engaged with a corresponding end of the fixed member, and a distance measured along the adjustable member from one connected end to the other connected end may be configured to be adjustable, such that a perimeter of a shape defined by the frame is adjustable. The device may be adjusted by adjusting the perimeter of the shape defined by the frame so as to allow the device to conform to a shape of the mitral valve being treated for improving opening or closure of the mitral valve.

Adjusting the size of the device may, in some cases, comprise actuating an adjustment mechanism of the frame. The adjustment mechanism may be configured to engage slotted ends of a cinching member extending through the fixed member and the adjustable member, and actuation of the adjustment mechanism may serve to move the cinching member with respect to the fixed member and the adjustable member. Adjusting the size of the device may comprise enlarging the size of the device by applying an axial force to the adjustment mechanism while actuating the adjustment mechanism. The frame may comprise at least one hinge proximate adjoining ends of the adjustable member and the fixed member, and the method may further comprise adjusting an elevation of the frame with respect to a reference plane passing through the fixed member by actuating the at least one hinge.

Actuating the at least one hinge may comprise applying a pinching force to the at least one hinge, and the at least one hinge may be configured to allow adjustment of the elevation to an angle between approximately 0° and approximately 20°.

In some cases, the frame may comprises a malleable material, and the method may further comprise adjusting an elevation of the frame with respect to a reference plane passing through the fixed member by applying pressure to portions of the frame.

BRIEF DESCRIPTION OF THE DRAWINGS

Figure 1:
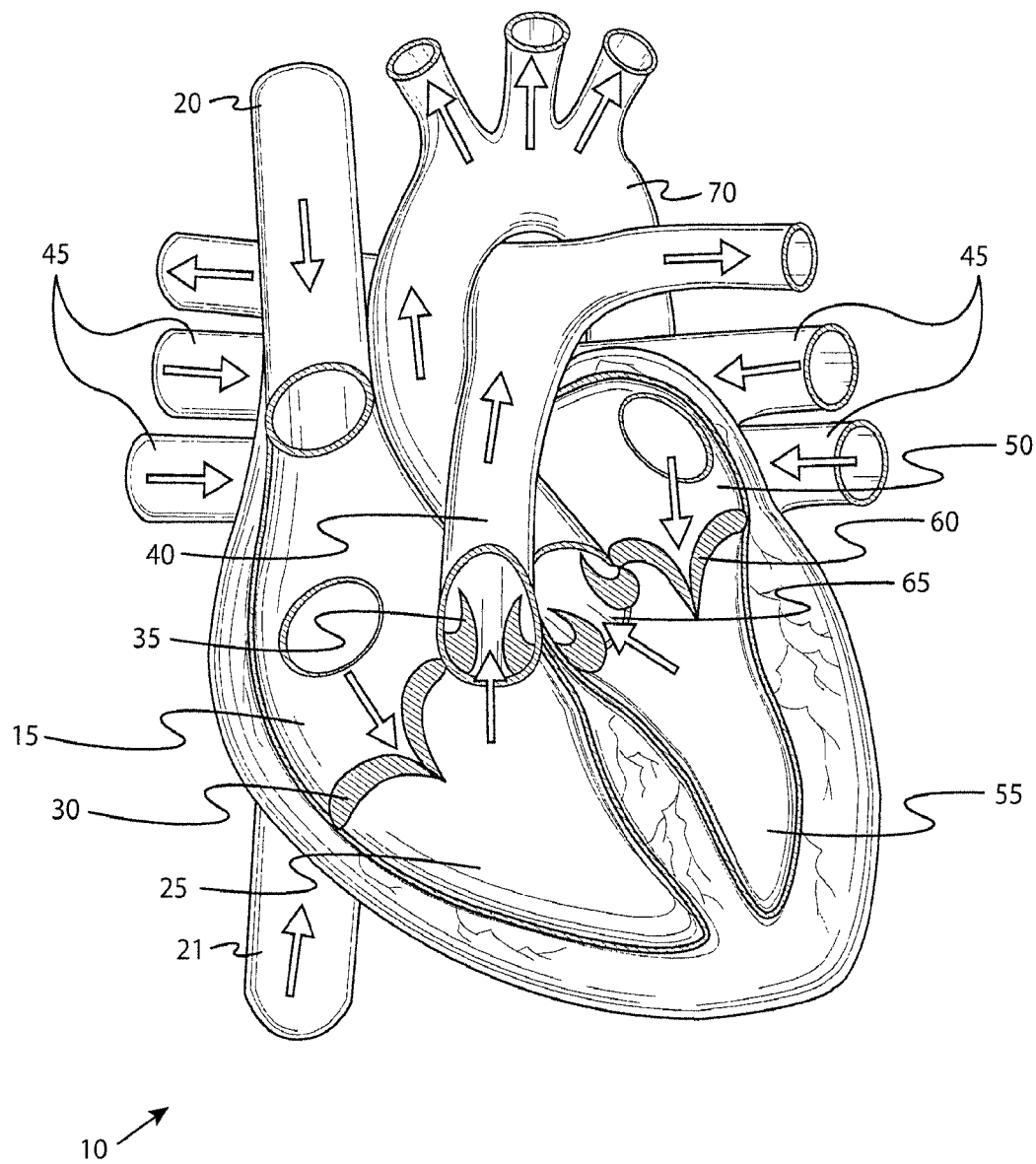
Figure 2:
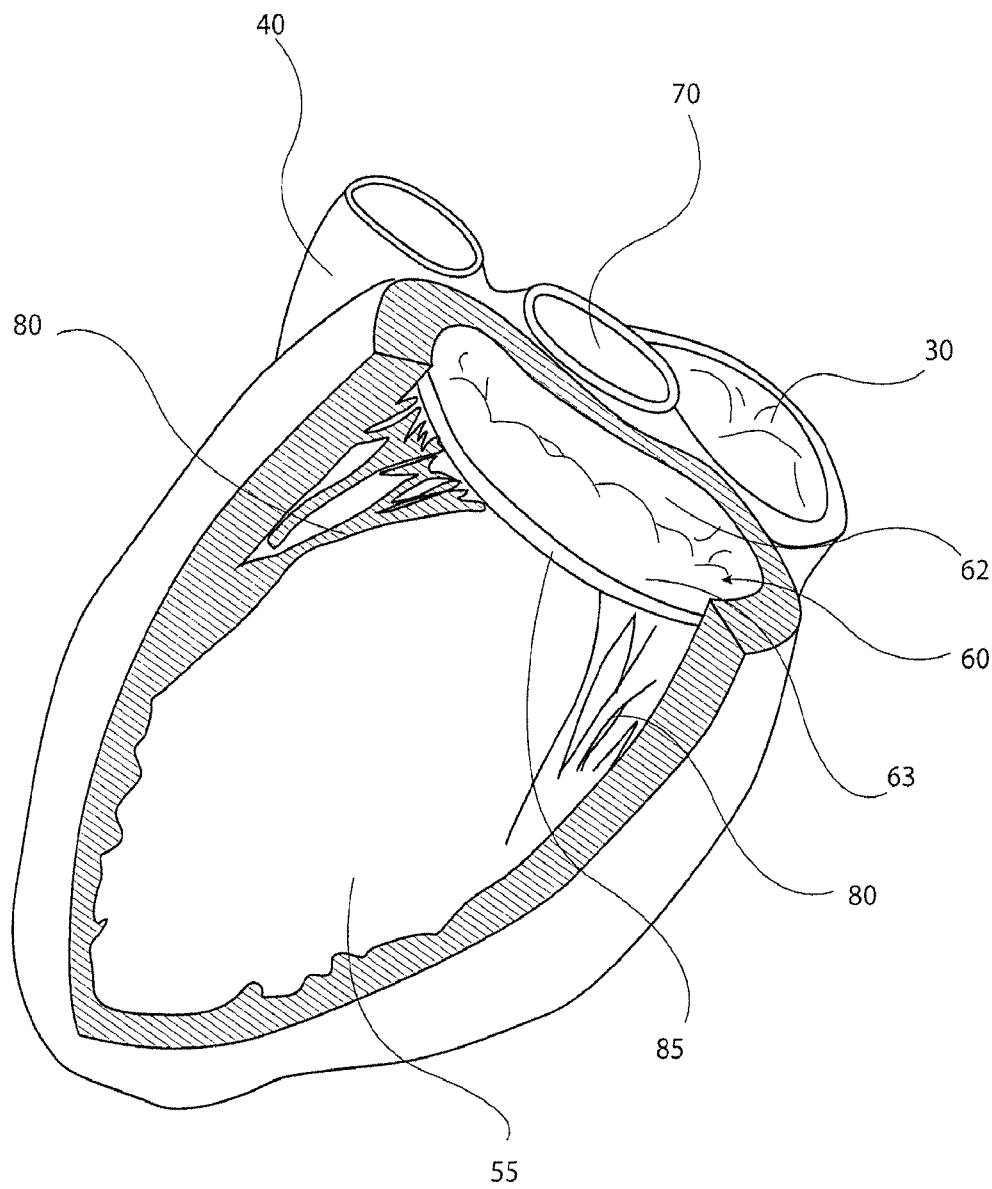
Figure 3:
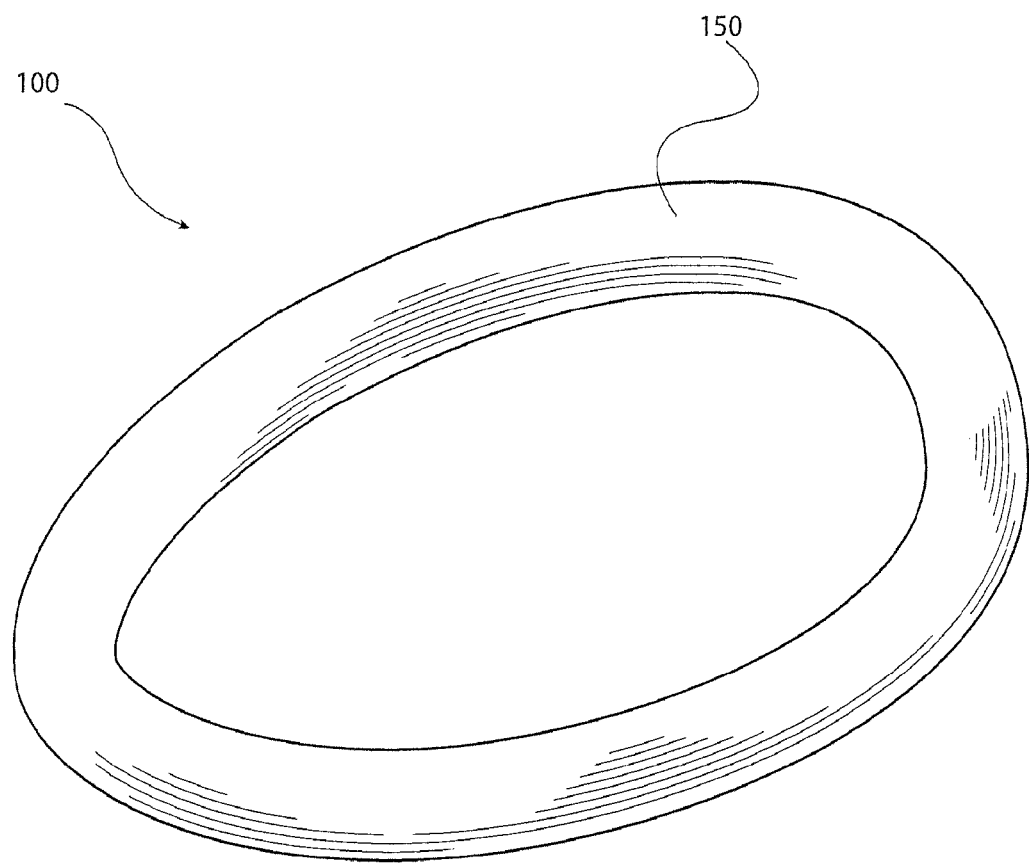
Figure 4:
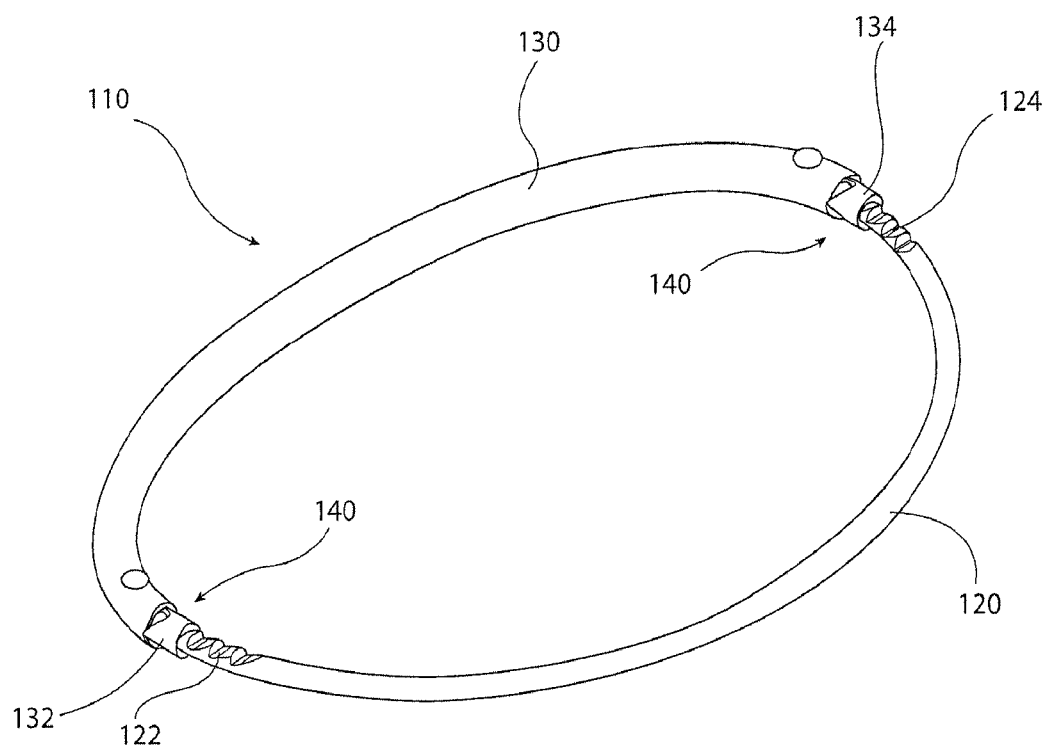
Figure 7:
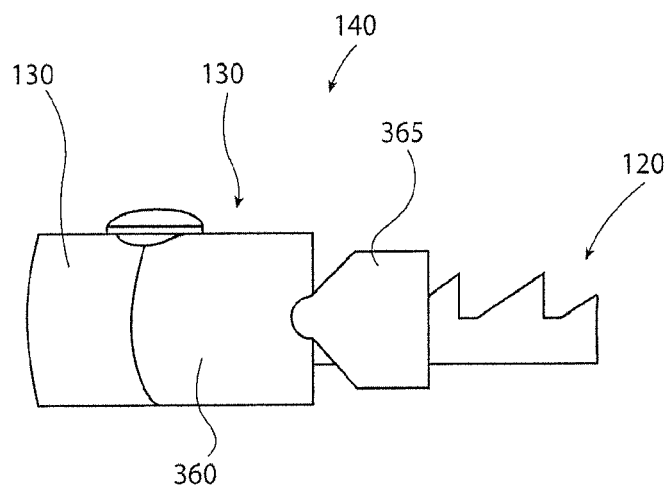
Figure 5A:
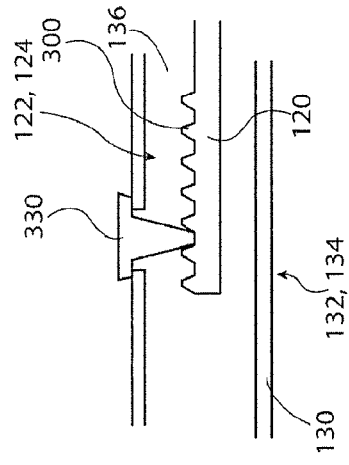
Figure 5B:
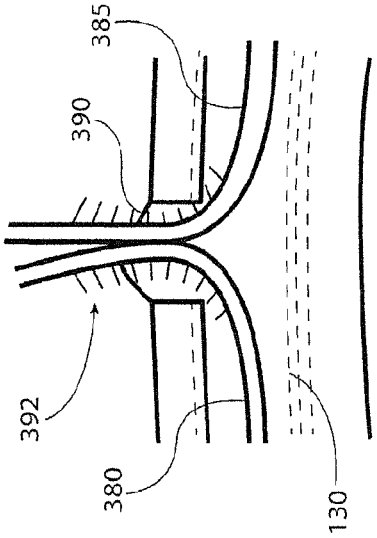
Figure 6:
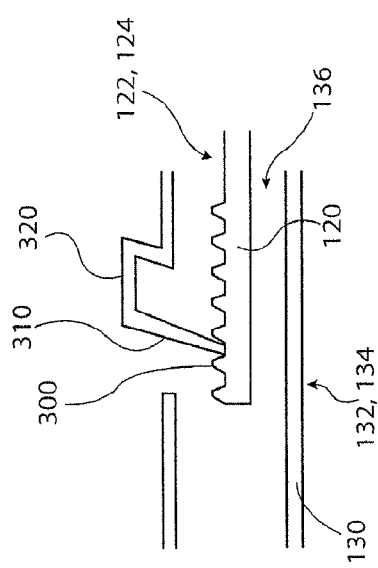
Figure 10A:
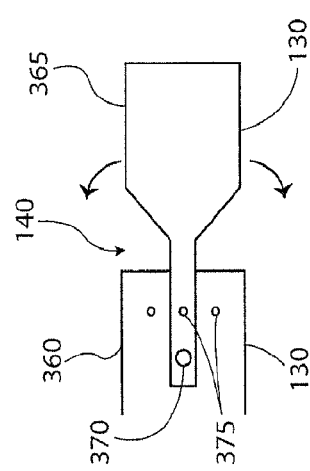
Figure 8:
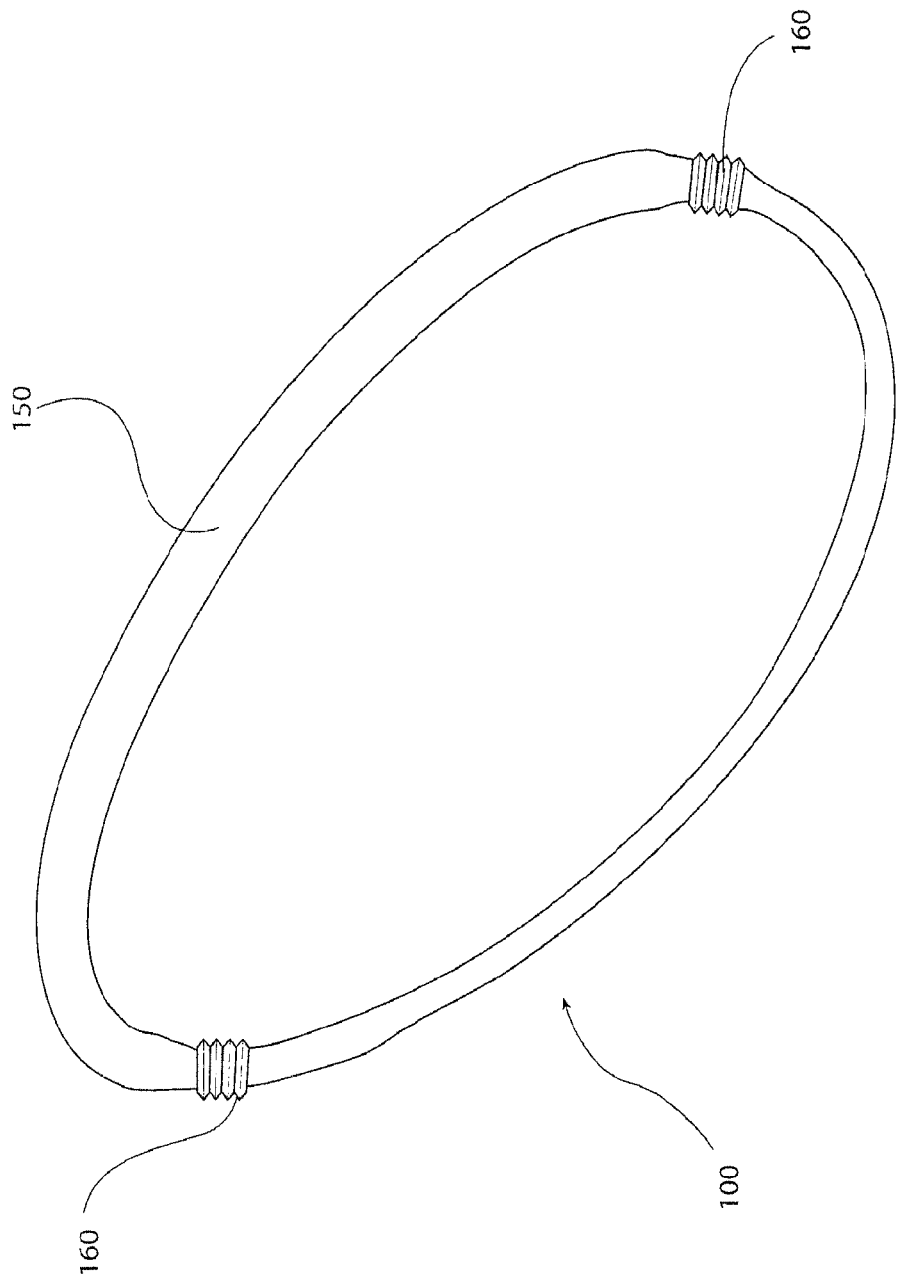
Figure 9:
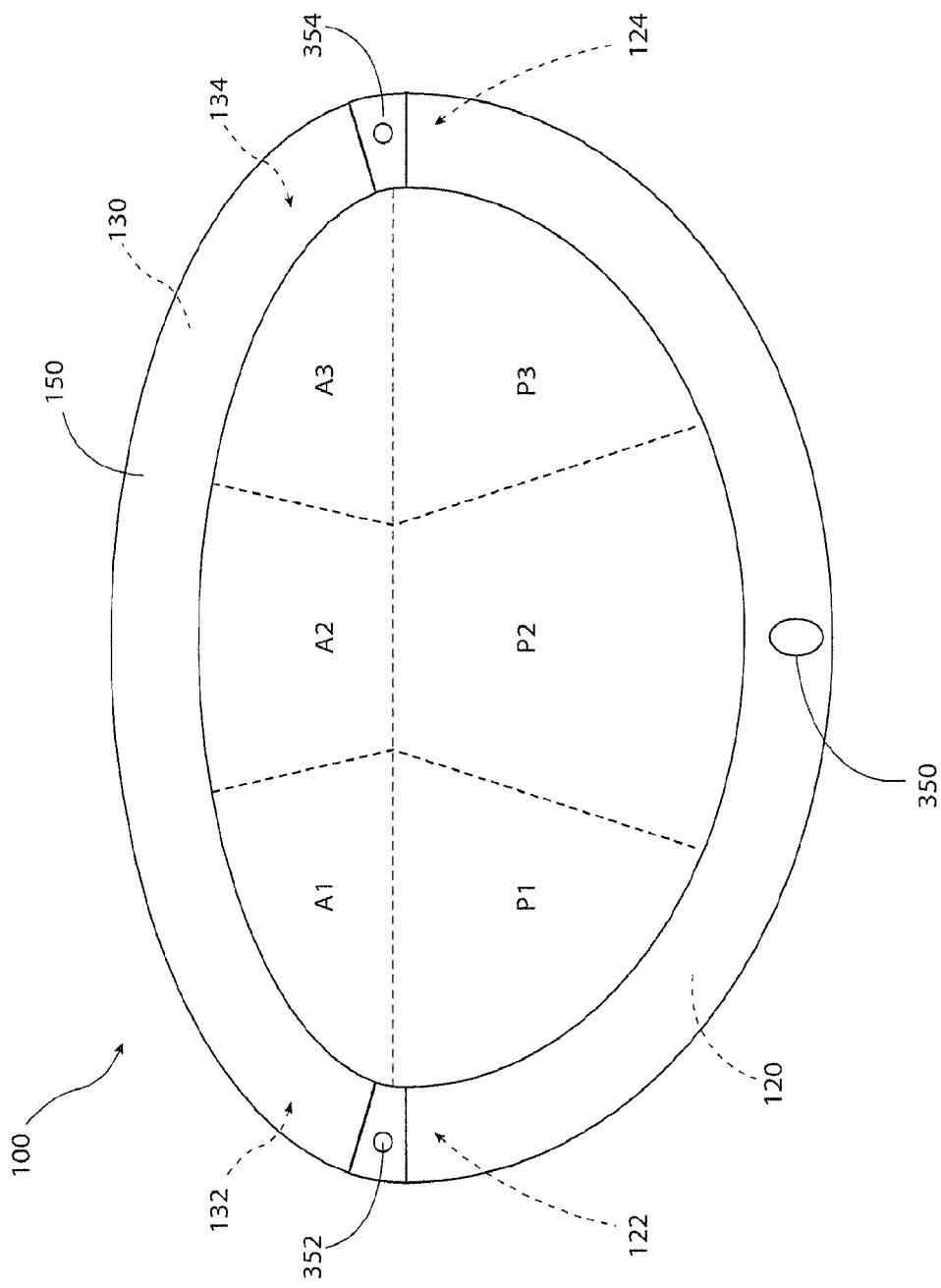
Figure 10:
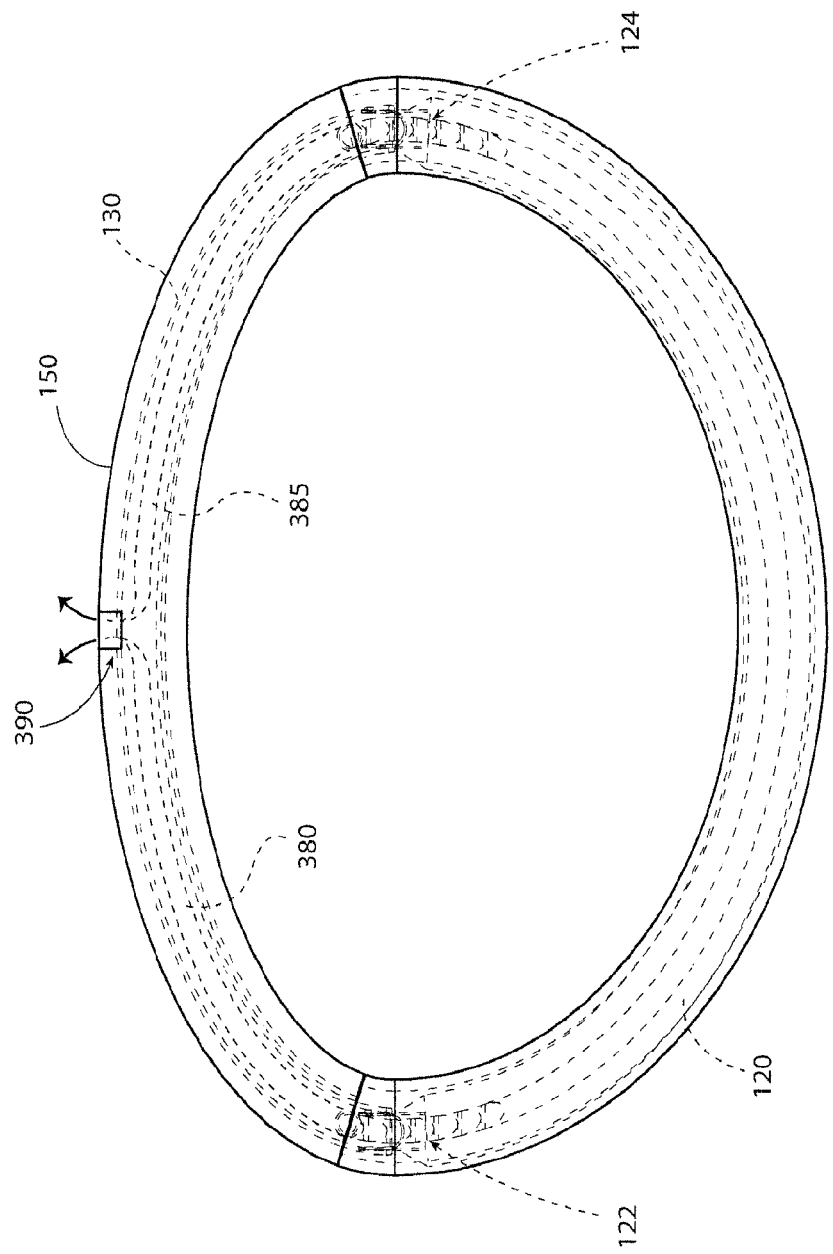
Figure 11:
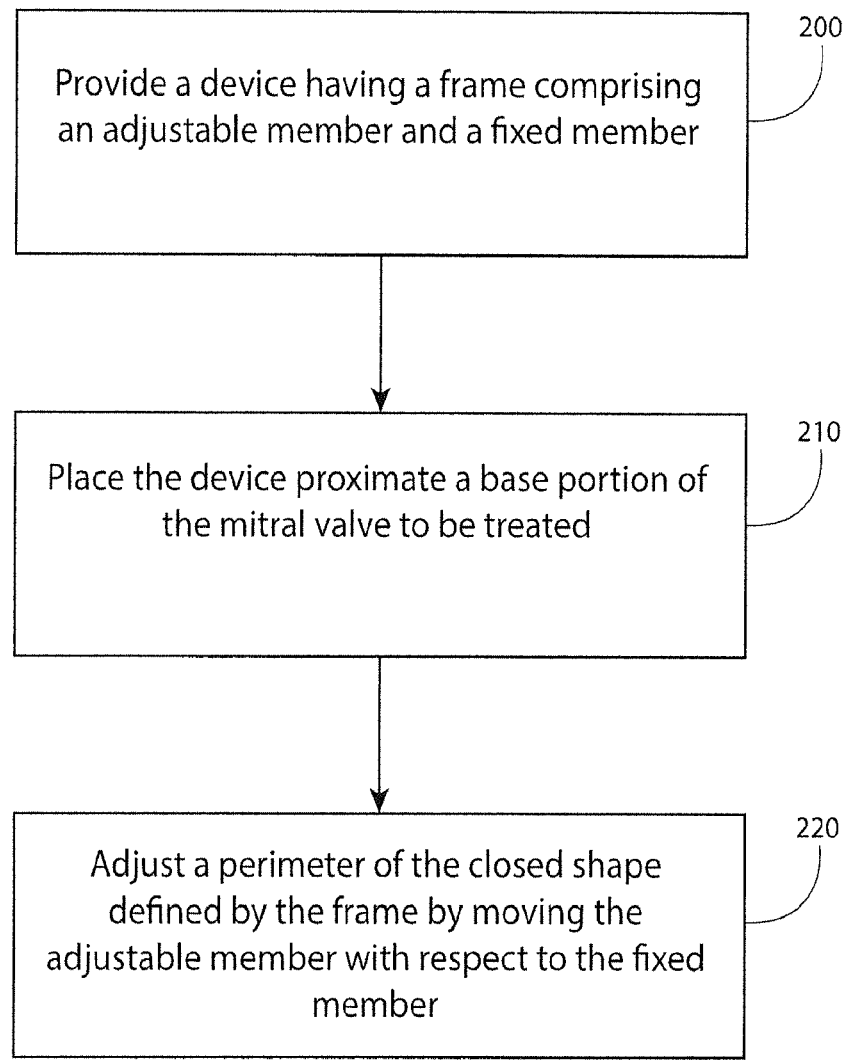
Figure 12:
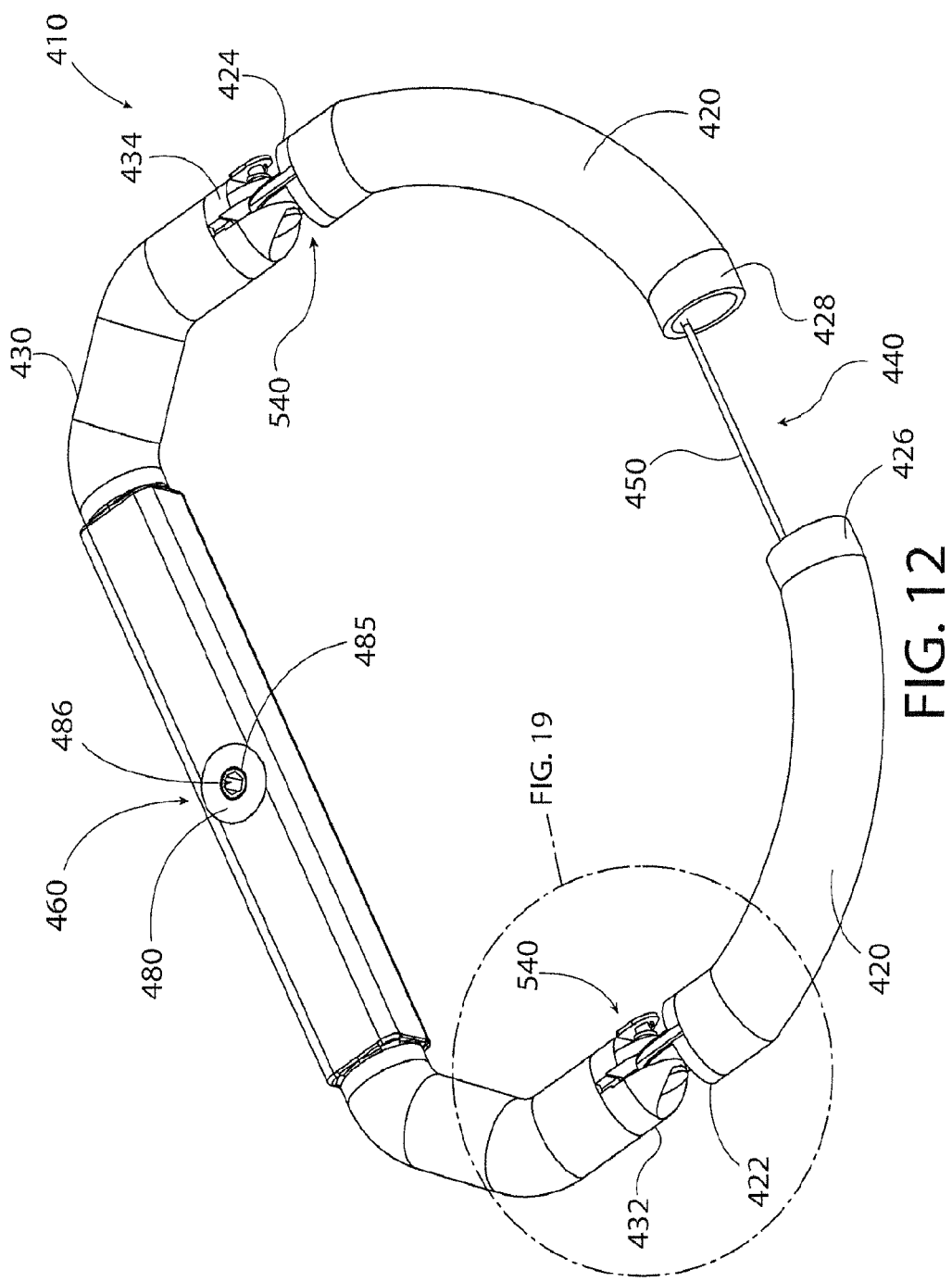
Figure 13:
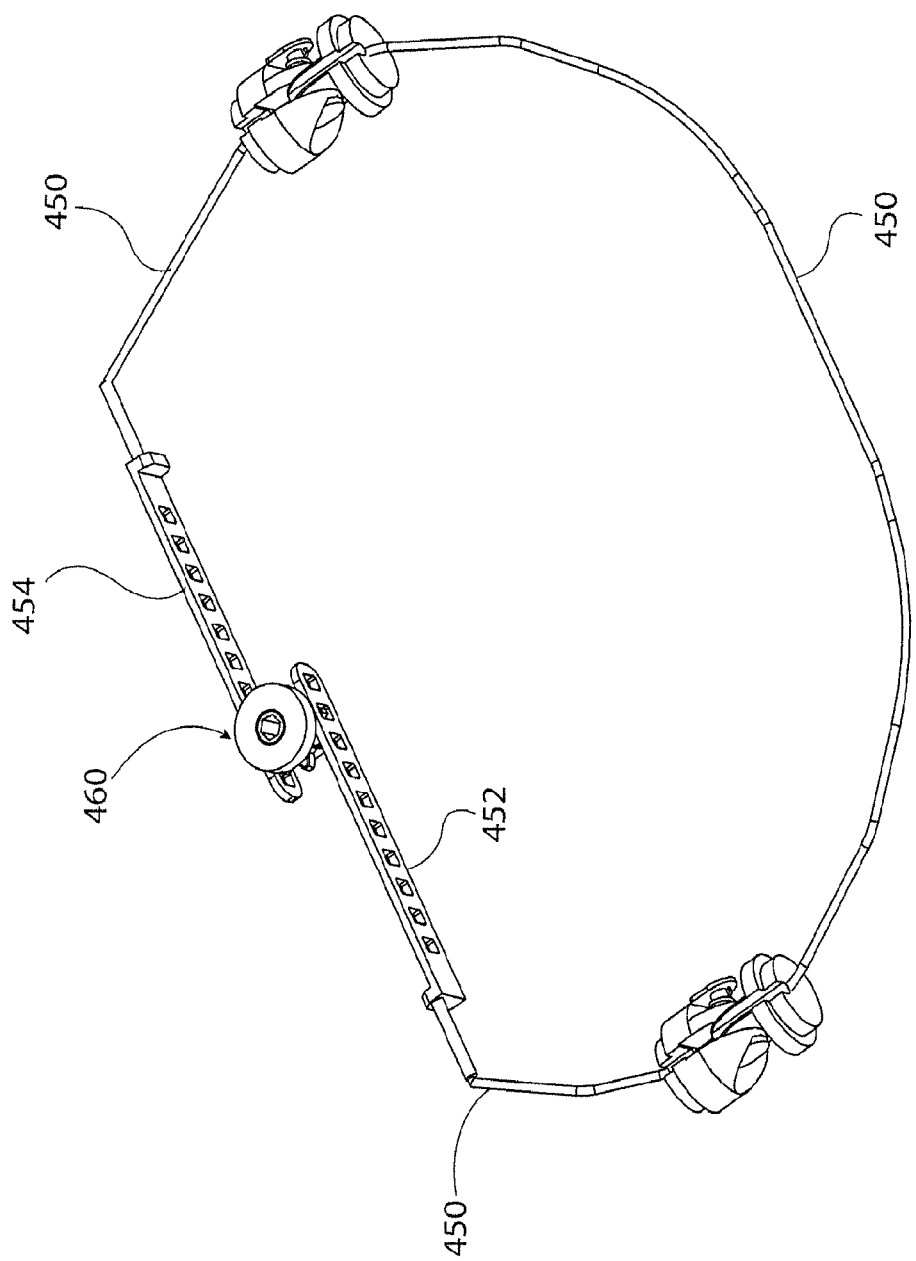
Figure 14:
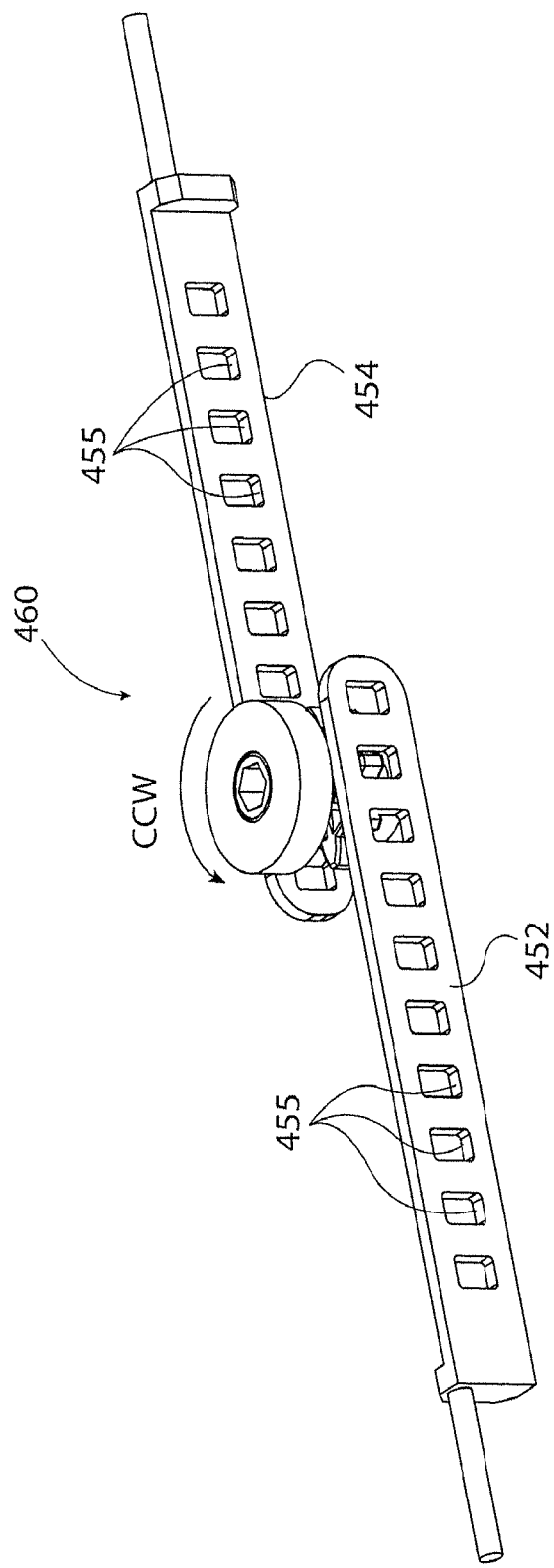
Figure 15:
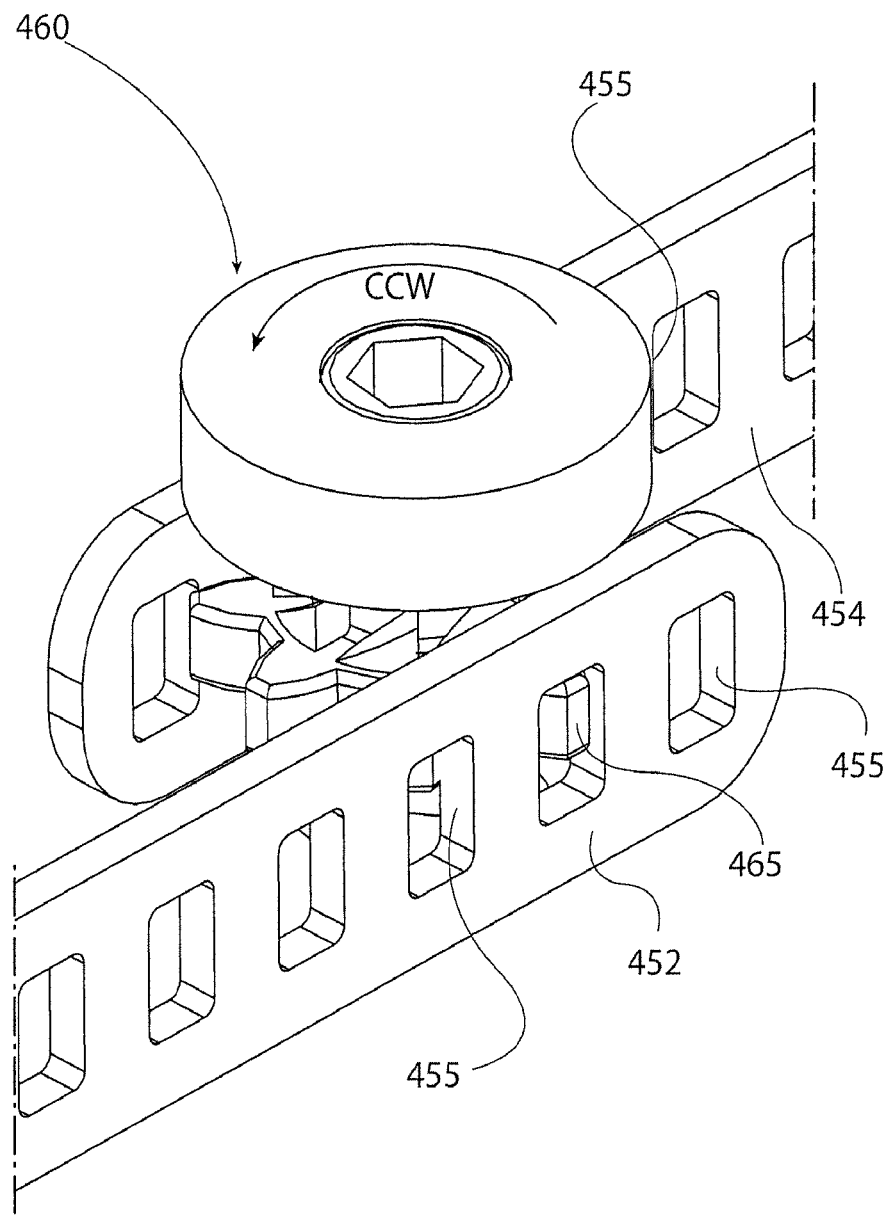
Figure 16:
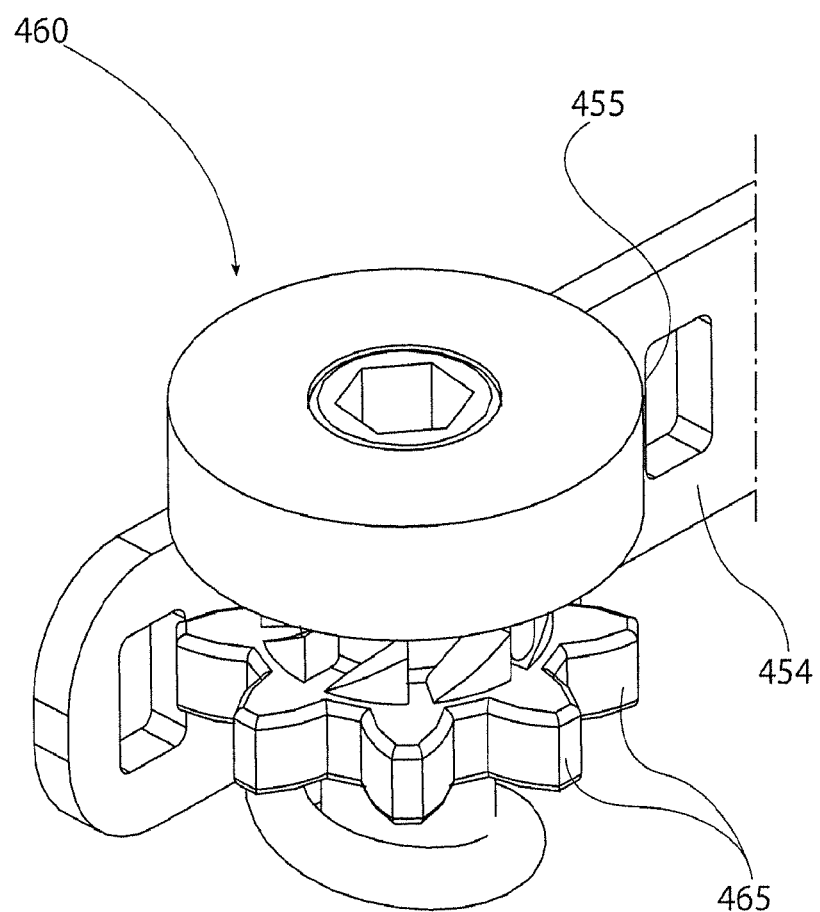
Figure 17:
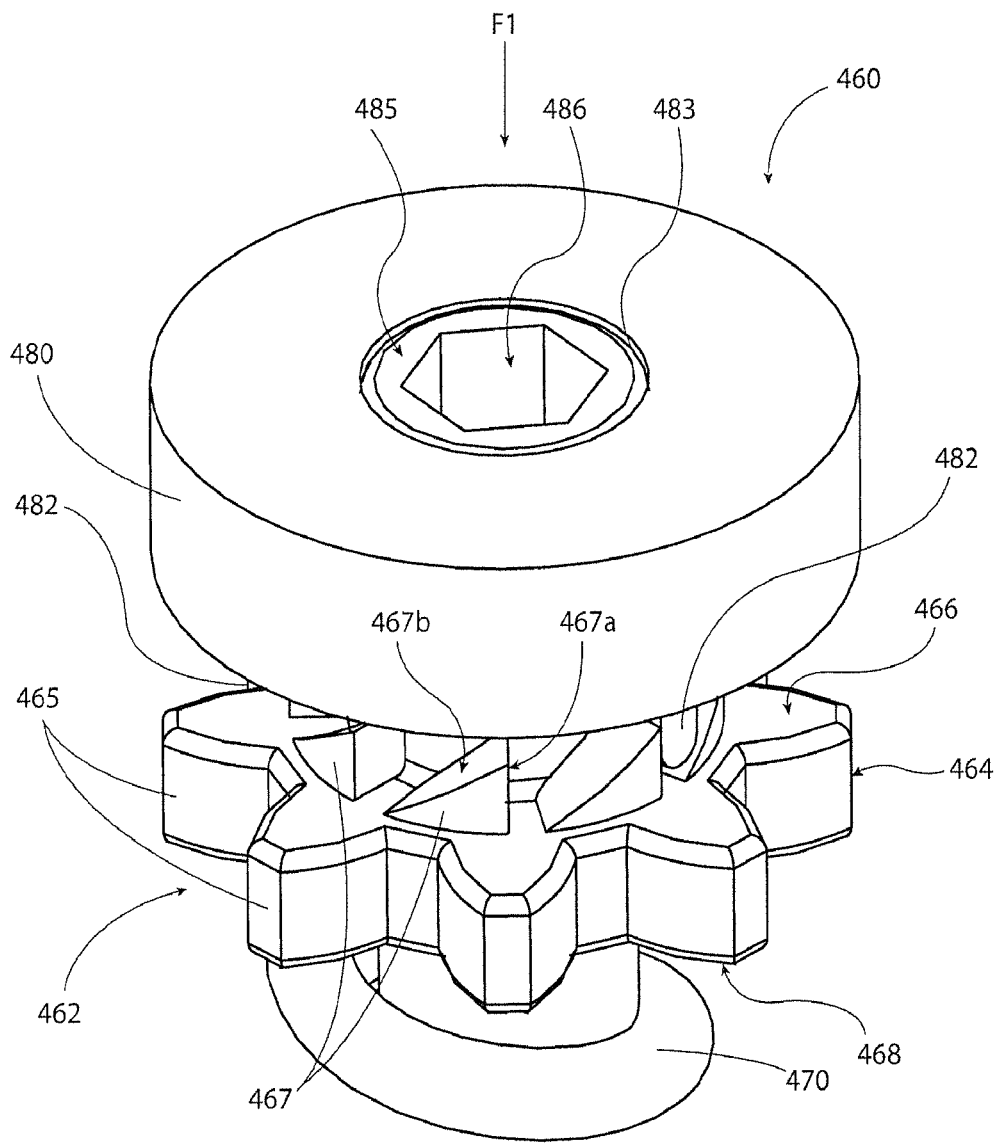
Figure 17A:
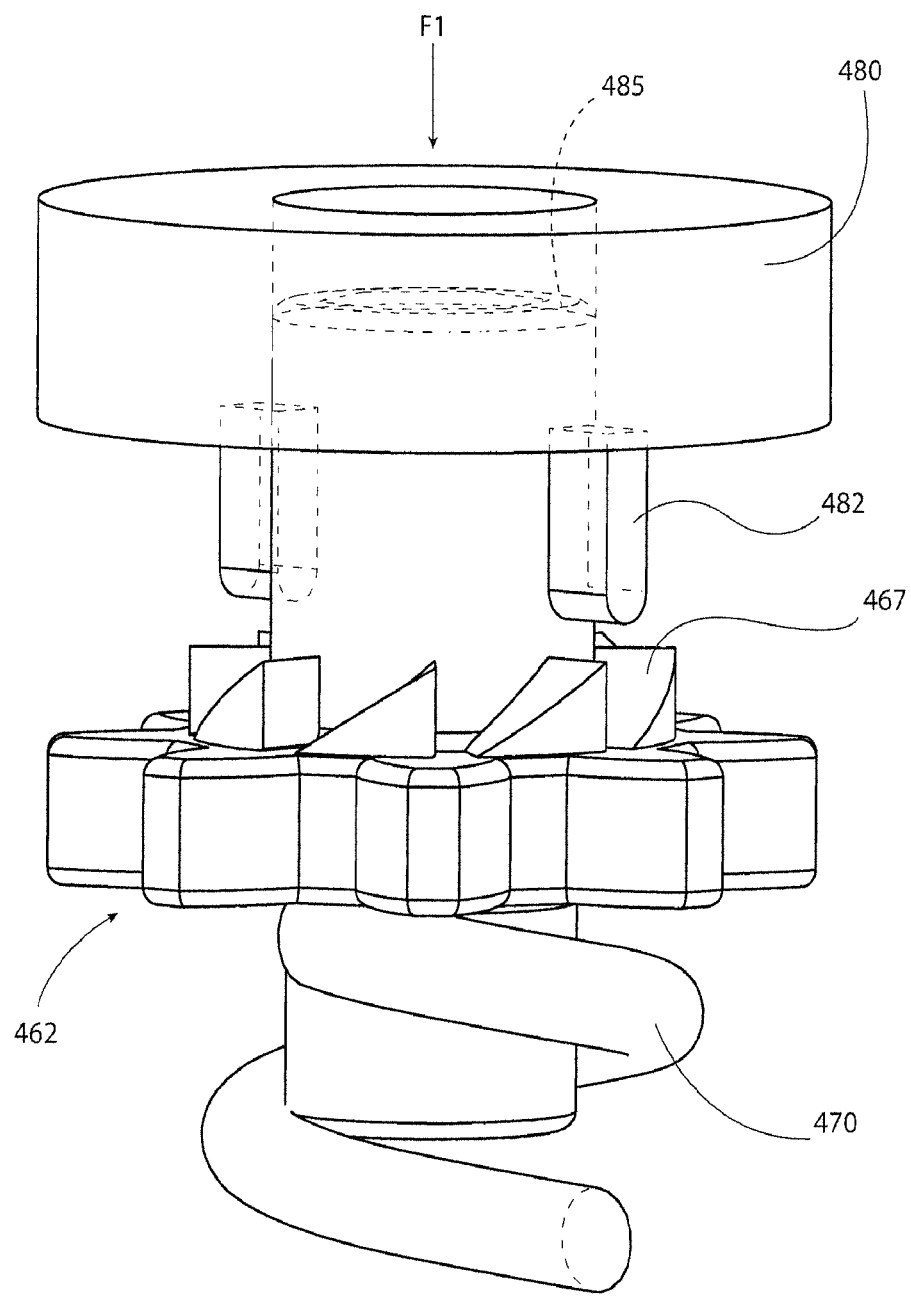
Figure 18:
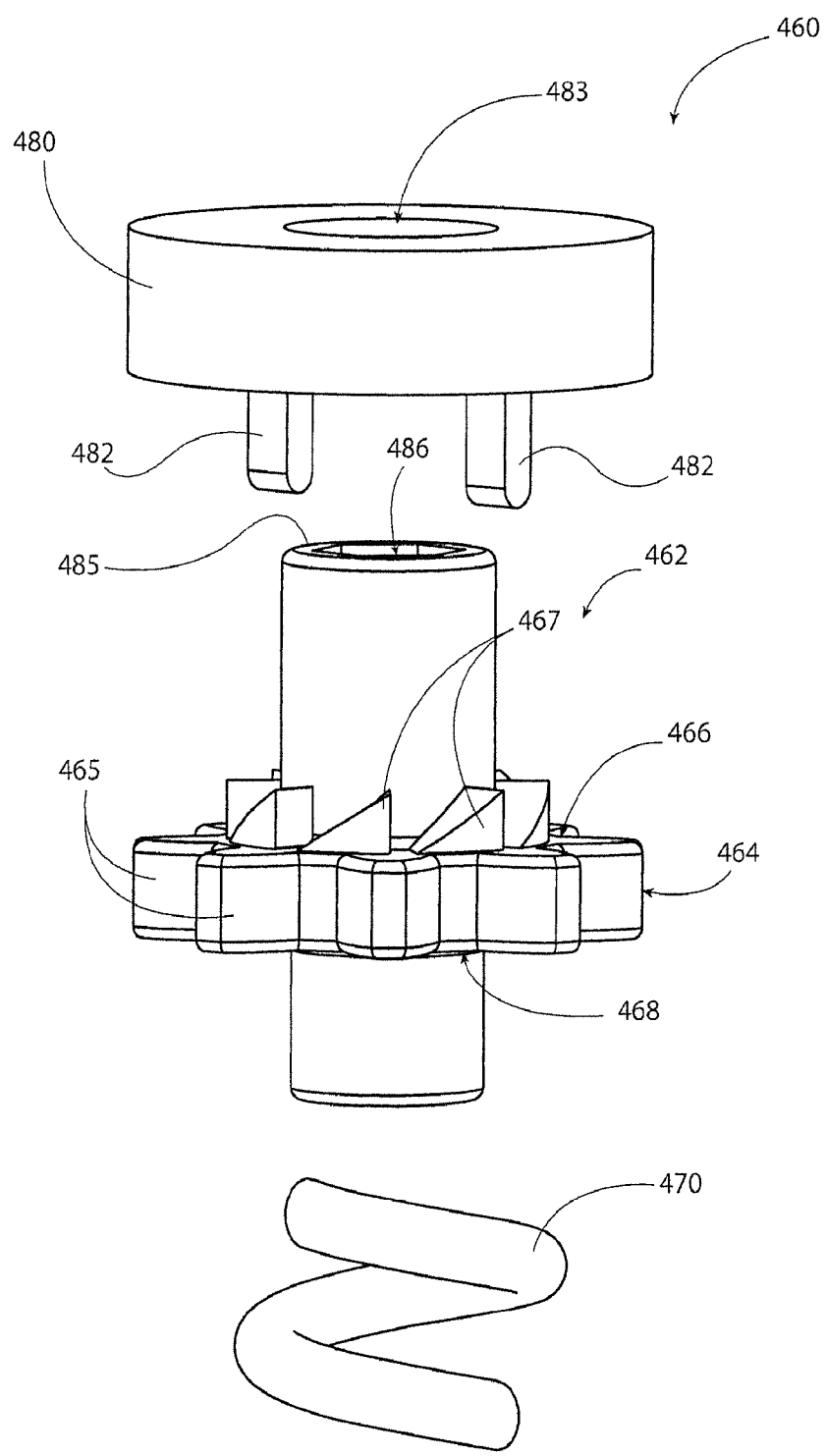
Figure 19:
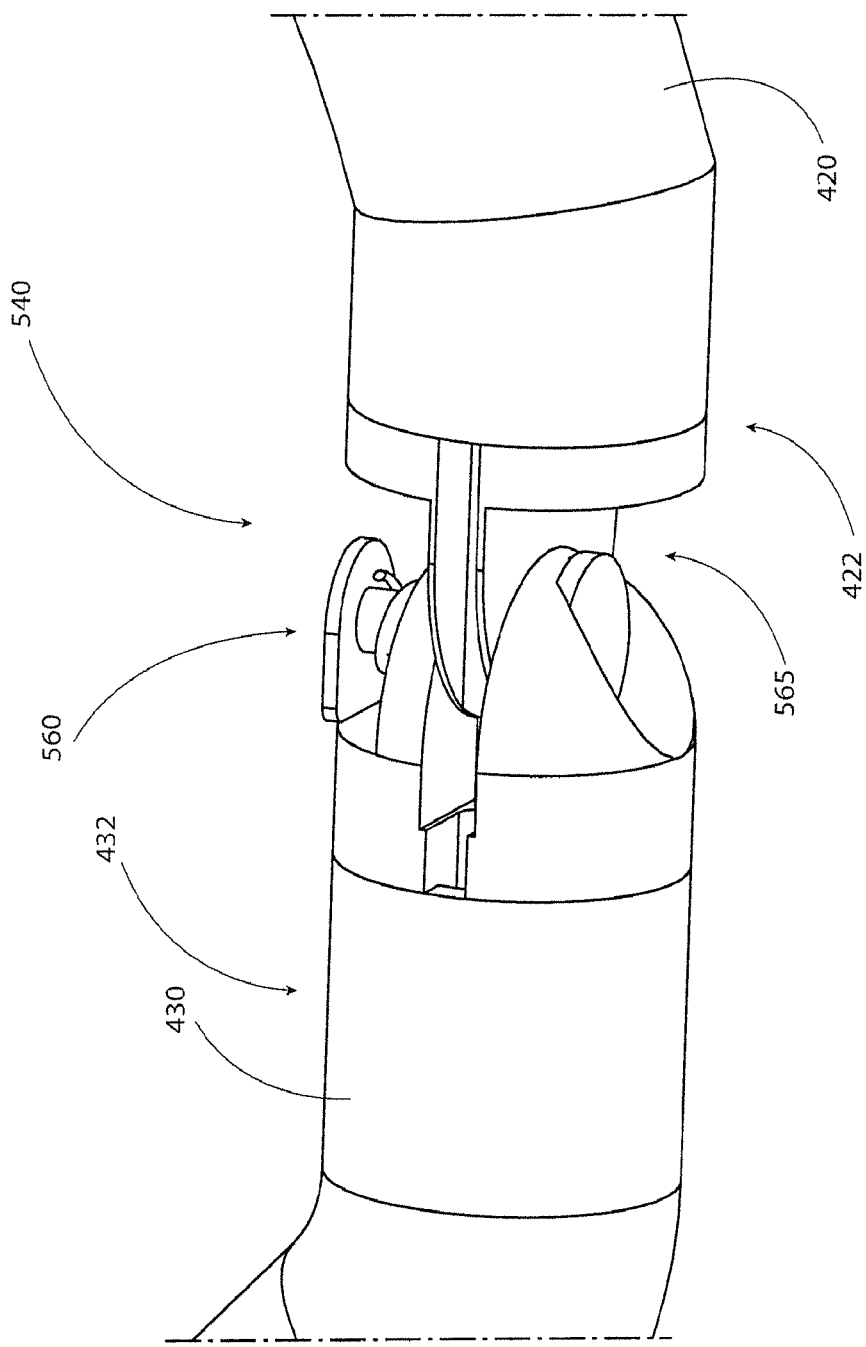
Figure 20:
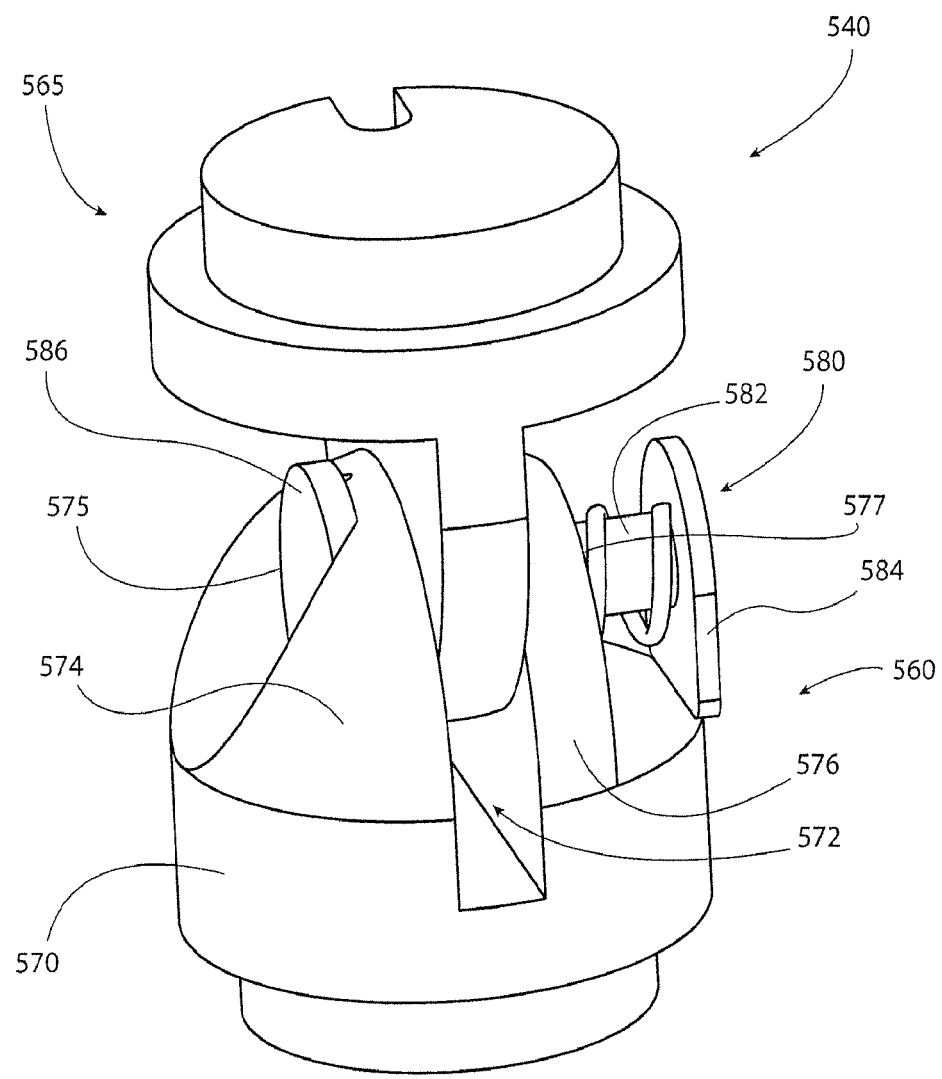
Figure 21:
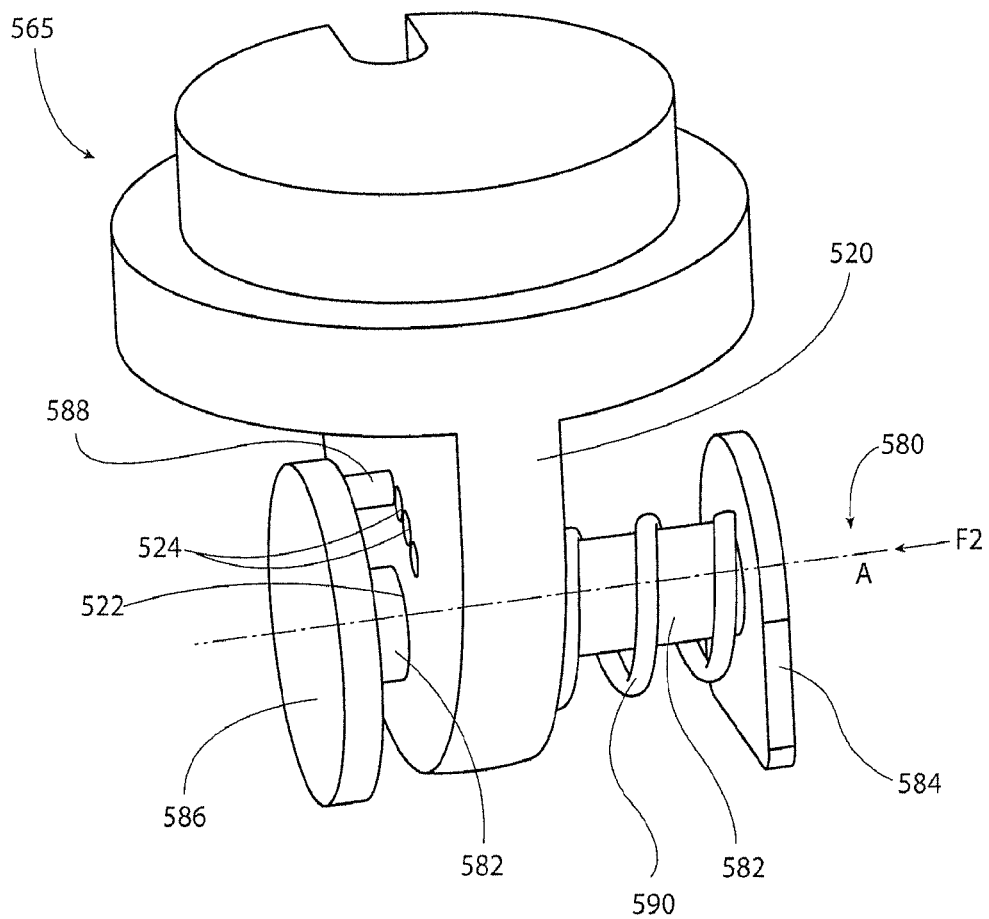
Figure 22:
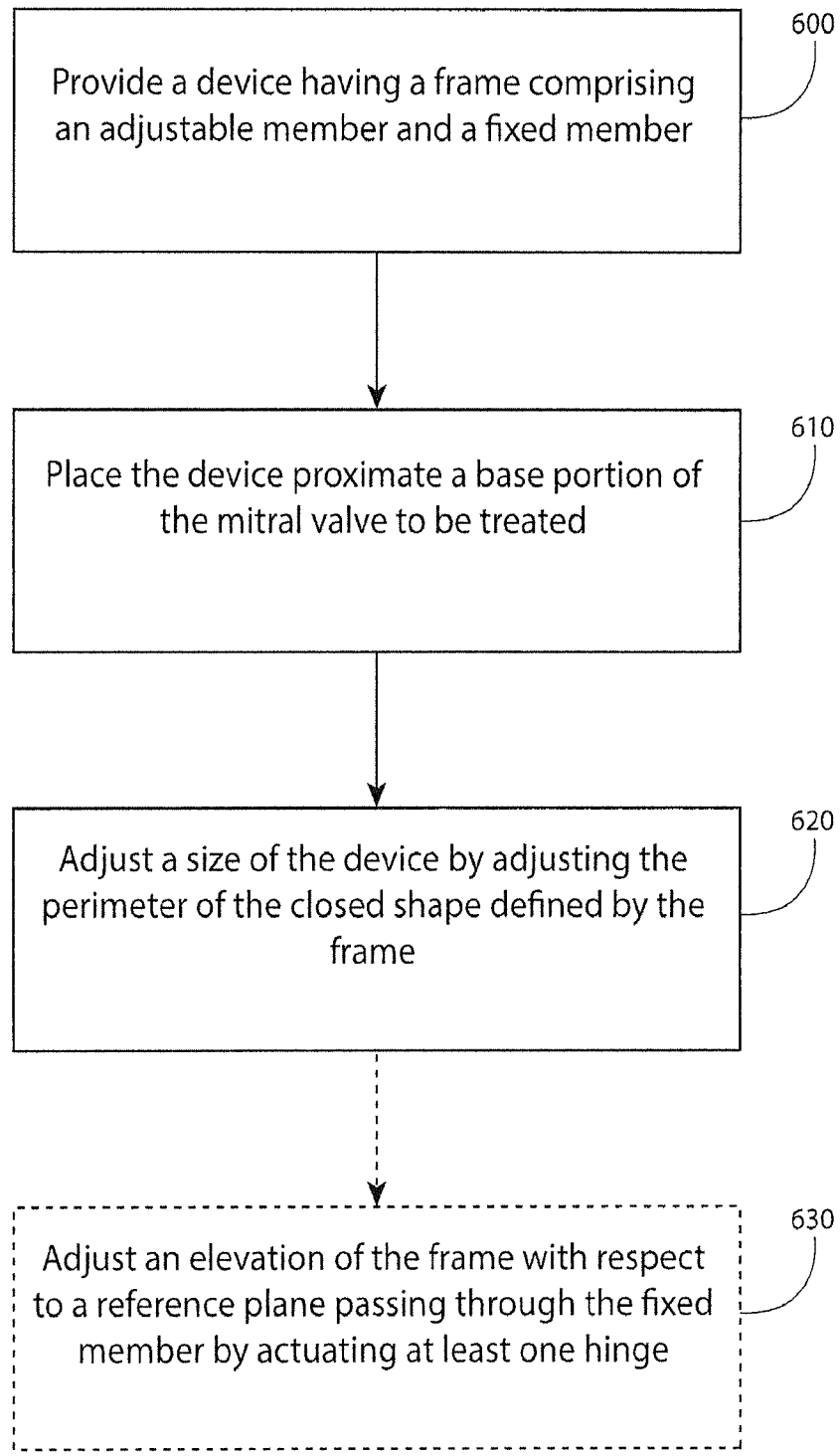

Having thus described the invention in general terms, reference will now be made to the accompanying drawings, which are not necessarily drawn to scale, and wherein:

FIG. 1 shows a schematic representation of a heart illustrating its various chambers and valves;

FIG. 2 shows a perspective view of a left ventricle of the heart and a mitral valve;

FIG. 3 illustrates a perspective schematic representation of a device for treating the mitral valve in accordance with an exemplary embodiment of the present invention;

FIG. 4 illustrates a perspective schematic representation of a frame of a device for treating the mitral valve in accordance with an exemplary embodiment of the present invention;

FIG. 5A illustrates a schematic view of a locking mechanism at an interface of the adjustable member and the fixed member of the frame in accordance with an exemplary embodiment of the present invention;

FIG. 5B illustrates a schematic view of a locking mechanism at an interface of the adjustable member and the fixed member of the frame in accordance with another exemplary embodiment of the present invention;

FIG. 6 illustrates a schematic view of a hinge mechanism in accordance with an exemplary embodiment of the present invention;

FIG. 7 shows a close up view of a hinge of the device in accordance with another exemplary embodiment of the present invention;

FIG. 8 shows a perspective schematic representation of a device having an outer covering over the frame in accordance with another exemplary embodiment of the present invention;

FIG. 9 shows a top view of the device with adjustable zones in accordance with another exemplary embodiment of the present invention;

FIG. 10 shows a top view of the device with extensions for remotely cinching the device in accordance with another exemplary embodiment of the present invention;

FIG. 10A shows a close up view of an access port for the extensions of FIG. 10 in accordance with another exemplary embodiment of the present invention;

FIG. 11 illustrates a flowchart of a method of treating a mitral valve using a device in accordance with an exemplary embodiment of the present invention;

FIG. 12 illustrates a perspective schematic representation of a frame of a device for treating the mitral valve in accordance with another exemplary embodiment of the present invention;

FIG. 13 illustrates a perspective schematic representation of a cinching member of the frame of FIG. 12 in accordance with an exemplary embodiment of the present invention;

FIG. 14 illustrates a detail perspective schematic representation of an adjustment mechanism of the cinching member of FIG. 13 in accordance with an exemplary embodiment of the present invention;

FIG. 15 illustrates a close-up view of the adjustment mechanism of FIG. 14 in accordance with an exemplary embodiment of the present invention;

FIG. 16 illustrates the adjustment mechanism of FIG. 15 with a slotted end of the cinching member removed for explanatory purposes in accordance with an exemplary embodiment of the present invention;

FIG. 17 illustrates the adjustment mechanism of FIG. 15 in a first axial position in accordance with an exemplary embodiment of the present invention;

FIG. 17A illustrates the adjustment mechanism of FIG. 15 in a second axial position in accordance with an exemplary embodiment of the present invention;

FIG. 18 illustrates an exploded view of the adjustment mechanism of FIG. 15 in accordance with an exemplary embodiment of the present invention;

FIG. 19 illustrates a hinge for adjusting an elevation of the device of FIG. 12 in accordance with an exemplary embodiment of the present invention;

FIG. 20 illustrates a close-up view of the hinge of FIG. 19 in accordance with an exemplary embodiment of the present invention;

FIG. 21 illustrates the hinge of FIG. 20 with the first hinge portion housing removed for explanatory purposes in accordance with an exemplary embodiment of the present invention; and FIG. 22 illustrates a flowchart of a method of treating a mitral valve using a device in accordance with another exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Although the examples described herein refer to mitral valve defects such as stenosis and regurgitation, embodiments of the described invention may be used to treat various mitral valve defects affecting the proper opening and/or closure of a mitral valve, both congenital and developed due to disease or other environmental factors.

With reference to FIG. 1, the path of circulation of blood through the heart 10 will be described. In the human body, deoxygenated blood enters the right atrium 15 of the heart 10 via the superior vena cava 20 (from the upper half of the body) and the inferior vena cava 21 (from the lower half of the body). Once the right atrium 15 is full of blood, the pressure difference between the right atrium and the right ventricle 25 causes the tricuspid valve 30 to open, allowing blood to flow into the right ventricle 25. As the right ventricle 25 contracts, blood is pushed through the pulmonary valve 35 and into the lungs via the pulmonary artery 40, where the blood is re-oxygenated. Oxygenated blood from the lungs can then re-enter the heart 10 via the pulmonary veins 45 into the left atrium 50. The pressure differential between the left atrium 50 and the left ventricle 55 when the left atrium fills with blood then causes the mitral valve 60 to open, and blood is allowed to flow from the left atrium to the left ventricle. Finally, contraction of the left ventricle 55 forces the aortic valve 65 to open and pushes blood into the aorta 70, from which oxygenated blood is circulated through the vasculature.

Unlike the other heart valves 30, 35, and 65, which are tricuspid valves having three leaflets, the mitral valve 60 is a bicuspid valve having two leaflets—the anterior leaflet 62 and the posterior leaflet 63 (shown in FIG. 2). The leaflets 62, 63 are connected by a fibrous ring called the mitral annulus 85. When the left ventricle 55 contracts to pump blood into the aorta, the annulus 85 also contracts to reduce the area of the valve and facilitate complete closure of the leaflets 62, 63 in a healthy subject.

Small fibrous strings or cords called chordae tendineae run from the leaflets 62, 63 to the walls of the left ventricle 55. When the left ventricle 55 contracts, the pressure in the left ventricle is much greater than the pressure in the left atrium 50, and the leaflets 62, 63 of the mitral valve 60 thus have a tendency to evert (e.g., be pulled into the left atrium). When this happens, the chordae tendineae become tense and pull on the leaflets 62, 63, thereby preventing eversion and holding the leaflets in a closed position.

Proper functioning of the valves 30, 35, 60, and 65 is essential to proper blood flow through the heart 10. In some cases, however, whether due to congenital defects or disease, one or more of the valves may not open or close as it should. For example, the mitral valve 60 may suffer from stenosis, or a narrowing of the valve that keeps the valve from fully opening to allow blood to flow into the left ventricle 55. In other cases, the mitral valve 60 may not fully close (referred to as leakage or regurgitation). Both conditions are undesirable and can cause serious consequences to the body, such as atrial fibrillation, blood clots, and heart failure, among others.

Conventional methods of treating mitral valve problems (e.g., stenosis and regurgitation) range from medication to surgery. If the damage done to the mitral valve and the surrounding heart tissue by the defect is not severe enough to require valve replacement, the existing mitral valve may be repaired using surgical techniques. Typically, open-heart surgery is required to perform mitral valve repairs. During this type of surgery, the patient is placed on a heart-lung machine, and the heart may be cooled to slow or stop the heartbeat. Depending on the particular type and extent of the defect, the surgeon may reshape the valve by removing excess valve tissue, add support to the annulus 85 by adding tissue or other structure to the valve base, or attach the valve to nearby cord tissues.

In particular, cases in which the annulus 85 requires additional support to allow the leaflets 62, 63 to open and close properly are often addressed by sewing an annuloplasty ring to the valve base. Conventional rings may be made of metal, cloth, or tissue and may have a predefined size and/or shape. Thus, a surgeon must select a type and size of ring that the surgeon believes will produce the best results in the patient based on what is known about the anatomy of the mitral valve and its surroundings and the type and extent of the defect.

Accordingly, embodiments of the present invention provide an adjustable device for treating a mitral valve defect. In particular, embodiments of the device are configured to allow a size of the device (e.g., as defined by the perimeter of the device) to be adjusted (e.g., made larger or smaller) by a surgeon during a mitral valve repair procedure so as to achieve optimal results considering the actual mitral valve anatomy and the type and extent of the defect. Moreover, embodiments of the device may allow a surgeon to adjust a shape of the device to accommodate the actual shape of the patient's mitral valve and annulus, such as to adjust an elevation and/or curvature of the device as described below. In this way, the surgeon can configure the device in three dimensions (e.g., along the x-, y-, and z-axes) to achieve an optimal fit with the patient's mitral valve and maximize the support provided to the valve leaflets to effect better performance of the patient's valve. Embodiments of the device may also allow for adjustments to be made post-operatively. In other words, the device can be configured to fit with the valve in the particular patient's condition to allow the patient's valve to work as well as possible, recognizing that the patient's valve is not a healthy valve and is not functioning as a healthy valve.

With reference to FIGS. 3 and 4, a device 100 is provided comprising a frame 110 that includes an adjustable member 120 and a fixed member 130. The adjustable member 120 may define two ends 122, 124, and the fixed member 130 may define two ends 132, 134. Each end 122, 124 of the adjustable member 120 may be engaged with a corresponding end 132, 134 of the fixed member 130 to form a closed shape, such as an oval, as shown. Moreover, at least one end 122, 124 of the adjustable member 120 may be configured to be adjustably received by the corresponding end 132, 134 of the fixed member 130, such that a perimeter of the closed shape defined by the frame 110 (e.g., the circumference of the oval) is adjustable. In other words, one or both ends 122, 124 of the adjustable member 120 may be received by the corresponding end 132, 134 of the fixed member 130 to varying extents such that the perimeter may be decreased or increased, as needed to fit the opening of the patient's valve.

For example, referring to FIGS. 5A and 5B, the fixed member 130 may comprise a tubular member defining a channel 136 therethrough, and the at least one end 122, 124 of the adjustable member 120 may be configured to be adjustably received within the corresponding end 132, 134 of the tubular member via the channel. By moving one or both ends 122, 124 of the adjustable member 120 farther into the channel at the corresponding end 132, 134 of the tubular component of the fixed member 130, the surgeon can make the perimeter of the frame 110 smaller. Conversely, by withdrawing the respective end 122, 124 out of the corresponding end 132, 134 of the fixed member 130, the surgeon can make the perimeter of the frame 110 larger. In this way, the device may be configured to be positioned proximate a base portion of a mitral valve, and a perimeter of the device may be configured to be adjusted to fit the mitral valve being treated so as to improve the opening and/or closing of the mitral valve. In some embodiments, the fixed member 130 and the adjustable member 120 may both be tubular, so as to provide a tube-within-a-tube structure, whereas in other embodiments the adjustable member 120 may be a wire or other solid component (e.g., lacking a lumen) that is received by the fixed member.

Several mechanisms may be used to allow the size of the device 100 to be adjusted (e.g., made smaller or larger). In some embodiments, for example, a ratchet-mechanism may be used to engage the ends 122, 124 of the adjustable member 120 with the corresponding ends 132, 134 of the fixed member 130. Referring to FIG. 5A, for example, one or both ends 122, 124 of the adjustable member 120 may define a number of teeth 300, and the corresponding end 132, 134 of the fixed member 130 may define a pawl 310 that is configured to engage the teeth to hold the adjustable member in place. As the end 122, 124 of the adjustable member 120 is pushed into the corresponding end 132, 134 of the fixed member 130 (e.g., to make the device smaller), the pawl 310 may ride up a sloped surface of the engaged tooth 300 to engage the next adjacent tooth. At the same time, however, the pawl 310 may prevent the end 122, 124 from being pulled out of the corresponding end 132, 134 of the fixed member when engaged with the teeth 300, locking the adjustable member 120 and the fixed member 130 in position with respect to each other.

To enlarge the size of the device 100, an unlocking surface 320 may be pressed by the surgeon (e.g., through an outer covering of the device, described below), which may serve to push the pawl 310 out of engagement with the teeth 300 and allow the surgeon to pull the end 122, 124 of the adjustable member 120 out of the corresponding end 132, 134 of the fixed member 130.

Alternatively, with reference to FIG. 5B, a plunger 330 may be provided that is configured to move into and out of engagement with the teeth 300, such as in a direction perpendicular to a longitudinal axis of the end 122, 124 of the adjustable member. The plunger 330 may be manipulated by the surgeon during placement of the device 100, such as through an outer covering of the device or via an extension (not shown) protruding out of the covering that the surgeon can grip and manipulate.

In still other embodiments, the device 100 may include one or more adjustment ports 350, 352, 354, shown in FIG. 9. Two of the adjustment ports 352, 354 may be located, for example, at commissures of the device (e.g., proximate the interface between the ends 122, 124 of the adjustable member 120 and the corresponding ends 132, 134 of the fixed member 130) and may be configured to receive a tool (e.g., an Allen wrench-type tool) for incrementally adjusting the size of the device 100 to make the device larger or smaller. The adjustments may be made, for example, via an internal gear (not shown) that is engageable by the tool via the ports 352, 354 and that, in turn, engages ratcheted surfaces of respective ends 122, 124, 132, 134 of the adjustable and fixed member 120, 130, such that turning the tool (and, thus, the gear) in one direction (e.g., clockwise) serves to draw the respective adjustable end 122, 124 into the corresponding fixed end 132, 134, making the device smaller, and turning the tool in the other direction (e.g., counterclockwise) serves to push the respective adjustable end out of the corresponding fixed end, making the device larger.

In this regard, anterior zones A1, A2, A3 and posterior zones P1, P2, P3 of the opening defined by the device 100 may be defined, as illustrated in FIG. 9, and adjustment of the size via one of the adjustment ports 352, 354 may serve to adjust a relative area of one or more of the zones proximate that particular port. For example, an adjustment made via the adjustment port 352 may serve to increase or decrease (depending on the direction in which the tool is turned) the area of posterior zone P1, while anterior zones A1, A2, and A3 and posterior zones P2 and P3 remain relatively unchanged. Similarly, adjustment of the adjustment port 354 may serve to increase or decrease (depending on the direction in which the tool is turned) the area of posterior zone P3, while anterior zones A1, A2, and A3 and posterior zones P2 and P1 remain relatively unchanged. Moreover, removal of the tool from engagement with the respective adjustment port 352, 354 may lock the relative positions of the adjustable member 120 and the fixed member 130 with respect to each other, such that no further changes in the size of the device occur.

A third adjustment port 350 may also be provided at a central location of the adjustable member 120, as shown in FIG. 9. In embodiments in which a third adjustment port 350 is provided, the adjustable member 120 may comprise a first portion and a second portion (not shown), and the first and second portions may have engaging ends that meet near the location of the third adjustment port 350 (e.g., halfway between the commissures). In this regard, the third adjustment port 350 may be configured to draw one or the other of the first and second portions towards the port to make the device 100 smaller or to push one or the other of the first and second portions away from the port to make the device larger. Accordingly, a pair of internal gears (not shown) may be provided as described above with respect to the adjustment ports 352, 354 of the commissures that are configured to engage ratcheted surfaces of the ends of the two portions. The engagement may occur in a manner such that twisting a tool configured to engage at least one of the internal gears via the adjustment port 350 in one direction (e.g., clockwise) may serve to adjust one of the portions (e.g., the portion of the adjustable member 120 associated with the size of posterior zones P3 and P2) while leaving the other portion of the adjustable member unaffected. Similarly, twisting the tool via the adjustment port 350 in the other direction (e.g., counterclockwise) may serve to adjust the other of the portions (e.g., the portion of the adjustable member 120 associated with the size of posterior zones P1 and P2) while leaving the other portion of the adjustable member unaffected. This may be accomplished, for example, via one or more gears that are only configured to engage other gears or ratcheted surfaces in one direction (e.g., slipping off and not engaging the gears or surfaces when moved in the non-engaging direction).

In still other some embodiments, the at least one end 132, 134 of the fixed member 130 that is configured to adjustably receive the corresponding end 122, 124 of the adjustable member 120 may comprise a filling, and the filling may be configured to resist movement of the adjustable member with respect to the tubular member. For example, the channel 136 of the tubular member may be filled with a polymer at one or both ends 132, 134, such that although a surgeon may be able to push the respective end 122, 124 of the adjustable member 120 into or pull the end out of the corresponding end 132, 134 of the tubular member, the polymer filling may substantially prevent the respective engaged ends from moving with respect to each other when no force is being applied. In this way, once the surgeon has adjusted a size of the device according to the patient's anatomy and specific needs, the frame 110 will have a tendency to remain in the adjusted configuration and will not change sizes again without further intervention by the surgeon.

Although the depicted embodiment of FIGS. 3 and 4 shows a fixed member 130 that is tubular, in other embodiments the fixed member may have other configurations. For example, the fixed member may have discrete tubular portions proximate the two ends 132, 134 within which the corresponding ends 122, 124 may be received. As another embodiment, the fixed member may comprise a plurality of rings or other arched members extending along the perimeter of the fixed member at least in the vicinity of each end 132, 134 through which the corresponding ends 122, 124 of the adjustable member may be received.

In other embodiments, the fixed member 130 and the adjustable member 120 may be configured such that the adjustment in the size of the device occurs through the movement of free ends of the adjustable member 120 rather than at the junction between the ends 122, 124 of the adjustable member 120 and the ends 132, 134 of the fixed member 130. With reference to FIG. 12, for example, another embodiment of a device 100 (shown in FIG. 3) for treating a mitral valve defect is shown. The device includes a frame 410 that includes an adjustable member 420 and a fixed member 430. The adjustable member 420 may include two connected ends 422, 424 that are configured to be engaged with corresponding ends 432, 434 of the fixed member 430. The adjustable member 420 in the embodiment of FIG. 12 may include free ends 426, 428 that are arranged opposite each other and thus define an adjustment space 440 therebetween. The frame 410 may thus define a conformable shape formed by the fixed member 430 and the adjustable member 420, and a perimeter of the shape may be defined by a line extending nominally along the fixed member 430 and the adjustable member 420 and across the adjustment space 440 from one free end 426 to the other 428. As described in greater detail below, the perimeter of the shape defined by the frame may be adjustable via the adjustability of a distance measured along the adjustable member 420 from one connected end 422 to the other connected end 424, such as by increasing or decreasing the size of the adjustment space 440 (e.g., the distance between the free ends 426, 428). The device may be configured to be positioned proximate a base portion of a mitral valve and the device may be configured to be adjusted to conform to a shape of the mitral valve being treated so as to improve opening or closure of the mitral valve.

Accordingly, in embodiments such as the embodiment shown in FIG. 12, each of the fixed member 420 and the adjustable member 430 may define a lumen. The frame 410 may further comprise a cinching member 450 that extends through the respective lumens of the fixed member 420 and the adjustable member 430, and the cinching member may be movable with respect to the fixed member and the adjustable member to adjust the perimeter of the shape (e.g., making the nominal diameter of the frame larger or smaller). In this regard, the two free ends 426, 428 of the adjustable member 420 may be configured to be moved with respect to each other in response to a corresponding movement of the cinching member 450. The cinching member 450 is shown with the surrounding fixed member 430 and adjustable member 420 removed for purposes of explanation in FIG. 13.

The cinching member 450 may comprise one or more wires that are attached to each other (e.g., via soldering or welding) to form a loop that defines the general shape of the frame and, by extension, the device. For example, in the depicted embodiment, two flat wires disposed in the fixed member 430 (shown in FIG. 12) may be attached (e.g., welded) to a round wire disposed in the adjustable member 420 (also shown in FIG. 12) and, in some cases, extending at least partially into the fixed member 430 via the respective lumens.

As depicted in FIG. 13, the cinching member 450 may comprise two slotted ends 452, 454 that are disposed within the fixed member 430 (shown in FIG. 12). The slotted ends 452, 454 may be ends of flat wires, as described above, into which slots 455 are cut (e.g., via laser cutting, etc.). The device may further comprise an adjustment mechanism 460 that is configured to be actuated by a user to engage the slotted ends 452, 454 of the cinching member 450 and move the slotted ends with respect to each other to adjust a length of the cinching member, thereby increasing or decreasing the distance between the free ends 426, 428 of the adjustable member 420 shown in FIG. 12. The adjustment mechanism 460 is shown in greater detail in FIGS. 14-18. In FIGS. 14 and 15, for example, the adjustment mechanism 460 is shown engaged with the slotted ends 452, 454 of the cinching member 450. In FIG. 16, one of the slotted ends 452 is removed, and in FIGS. 17, 17A, and 18 the adjustment mechanism 460 is shown in assembled (FIGS. 17 and 17A) and exploded (FIG. 18) configurations apart from the cinching member 450, for purposes of explanation.

With reference now to FIGS. 17 and 18, the adjustment mechanism 460 may comprise a gear 462. The gear 462 may have a first engaging surface 464 and a second engaging surface 466, where the first and second engaging surfaces are positioned approximately perpendicular to each other, as shown. The first engaging surface 464 may extend about an outer circumference of the gear 462 and may define radially extending gear teeth 465 that are configured to mesh with the slots 455 defined in the slotted ends 452, 454 of the cinching member 450, as shown in FIGS. 14-16. In this way, rotation of the gear 462 via a user's actuation of the adjustment mechanism 460, as described in greater detail below, may serve to move the slotted ends 452, 454 either towards or away from each other, depending on the direction of rotation of the gear. In the depicted embodiment, and with reference to FIGS. 14 and 15, rotation of the gear as a result of actuation of the adjustment mechanism 460 in the counterclockwise direction (represented by the arrow CCW) serves to move the slotted ends 452, 454 towards each other, thereby making the size (e.g., the nominal diameter) of the cinching member 450 (FIG. 13) and the frame 410 (FIG. 12) (and therefore the device) smaller. Actuation of the adjustment mechanism 460 in the opposite direction would similarly make the size of the cinching member 450, the frame 410, and the device larger by moving the slotted ends 452, 454 away from each other.

In some embodiments, the adjustment mechanism 460 may comprise a locking member 480 that allows the gear 462 to be rotated solely in a first direction (e.g., the counterclockwise direction CCW shown in FIGS. 14 and 15) when the gear is in a first axial position and in a second direction (e.g., the clockwise direction) when the gear is in a second axial position. In this regard, and with reference to FIGS. 17, 17A, and 18, the gear 462 may be configured to cooperate with a spring 470 that contacts an ungeared surface 468 of the gear, such that in a rest position (e.g., when the user is not actuating or contacting the adjustment mechanism), the gear 462 is in the first axial position, and the spring is uncompressed (or relatively uncompressed, as compared to when the gear is in the second axial position, described below).

The locking member 480 may be configured to engage the gear 462 via contact between locking protrusions 482 defined in the locking member 480, which extend toward the second engaging surface 466 of the gear 462, and ramped teeth 467 defined in the second engaging surface 466. In this regard, each ramped tooth 467 may include a locking surface 467a and a sliding surface 467b, shown in FIG. 17. When the gear 462 is in the first axial position, shown in FIG. 17, the locking protrusion 482 may be configured to engage the locking surface 467a of a corresponding ramped tooth 467, such that movement of the gear in the clockwise direction (in the depicted embodiment) is prevented.

An actuation end 485 of the gear 462, in which is defined an opening 486 configured to receive a sizing tool (e.g., an Allen wrench-type of tool, not shown), may be received through an opening 483 defined in the locking member 480. A user may thus actuate the adjustment mechanism 460 by inserting the sizing tool into the opening 486 in the actuation end 485 of the gear 462 and rotating the gear. In the passively locked configuration shown in FIG. 17, the user will only be able to rotate the gear in the counterclockwise direction (shown in FIGS. 14 and 15). This is because the locking protrusions 482 of the locking member 480 are able to slide along the corresponding sliding surfaces 467b of the ramped teeth 467 via rounded ends of the locking protrusions. The gear 462 may be movable independently of the locking member 480, as shown, and the movement of the locking protrusions 482 along the sliding surfaces may serve to push the gear against the force of the spring 470, compressing the spring somewhat as each ramped tooth is cleared. If the user attempts to rotate the gear 462 in the opposite direction (e.g., clockwise in this example), the gear will not move an appreciable amount due to the engagement of the locking protrusions 482 with the corresponding locking surfaces 467a of the ramped teeth 467, as shown in FIG. 17. Thus, in the configuration shown in FIG. 17, the user would only be able to make the size of the cinching member 450 (FIG. 13) smaller, decreasing the size of the device.

By applying an axial force F1, as depicted in FIG. 17, via the tool received in the opening 486, however, the user may push the gear 462 against the force of the spring 470 by a great enough distance (while the locking member 480 is not moved) so that the user may be able to rotate the gear 462 without causing engagement of the locking protrusions 482 with the ramped teeth 467, as shown in FIG. 17A. In this way, the user may be able to rotate the gear 462 in either direction and, by rotating the gear in the clockwise direction, may enlarge the size of the device by applying an axial force F1 to the adjustment mechanism 460 prior to rotationally actuating the adjustment mechanism and maintaining the axial force as the gear 462 is rotated. Once the actuation is complete, the user may remove the tool from the opening 486, and the gear 462 may return to the first axial position in which the actuation mechanism 460 is passively locked by virtue of the bias imparted by the spring 470.

In some embodiments, the device 100 may further be configured such that, in addition to being adjustable with respect to a circumference of the device, an elevation of the device or portions of the device is also adjustable. In this regard, a portion of the device corresponding to one of the leaflets of the mitral valve (e.g., the posterior leaflet) may be raised or lowered with respect to a nominal plane of the device (e.g., a plane defined by the portion of the device corresponding to the other of the leaflets of the mitral valve, such as the anterior leaflet in this example). In this way, the device 100 may be adjustable in multiple dimensions to accommodate the type of repair needed to effect an optimum closure of the patient's valve, such as to compensate for a prolapsed leaflet by raising such a leaflet up.

Accordingly, in some cases, with reference to FIGS. 4 and 12, the frame 110, 410 (or at least portions of the frame) may comprise a malleable material. For example, the frame 110, 410 or at least a portion of the frame, such as the adjustable member 120, 420 or portions thereof, may comprise a material that can be bent or shaped when a force is applied to it. Thus, in such embodiments, the surgeon may be able to bend or adjust the shape or elevation of the frame 110, 410 to accommodate the anatomy of the patient's mitral valve and surrounding tissue. The malleable portions may, for example, be provided near the commissures of the device. In other embodiments, the frame 110 may comprise a flexible material that is configured to flex and move in response to the force applied to the device once it is installed in the heart. Such flexibility may, for example, allow the device to accommodate contractions of the annulus 85 (FIG. 2) as the heart pumps blood through the different chambers of the heart. In some embodiments, the frame 110, 410 may comprise a metal alloy such as nitinol or stainless steel, or a polymer material.

In other cases, the elevation of the device may be adjusted via hinges provided near the commissures. Referring to FIGS. 6 and 7, for example, the frame 110 may, in some embodiments, comprise at least one hinge 140 proximate adjoining ends of the adjustable member 120 and the fixed member 130. In the depicted embodiment, the frame 110 includes two hinges 140 formed in a portion of the fixed member 130. In this regard, the respective end 132, 134 of the fixed member 130 may include a first hinge portion 360 and a second hinge portion 365, where the second hinge portion 365 is configured to receive the end 122, 124 of the adjustable member (e.g., as described above). As illustrated in FIG. 6, the first hinge portion 360 and the second hinge portion 365 may be pivotally connected via a pin 370. A series of locking pins 375 may be provided at predefined intervals within the first hinge portion 360 that are configured to engage a corresponding opening or concavity of the second hinge portion 365, such that the second hinge portion is held in place at a certain angle (which may be zero) with respect to the first hinge portion 360 based on which locking pin 375 is engaged. As a result, by selecting the appropriate locking pin 375, the second hinge portion 365 may be rotated above the pin 370 and the first hinge portion 360 to a desired one of the preset angles.

In other embodiments, such as the embodiment depicted in FIG. 12, the frame 410 may comprise at least one hinge 540 proximate adjoining ends 432, 422, 434, 424 of the adjustable member 420 and the fixed member 430. As noted above with respect to the embodiment of FIG. 3, the at least one hinge 540 may be configured to allow adjustment of an elevation of the frame 410 with respect to a reference plane passing through the fixed member 430. With reference to FIGS. 12 and 19, for example, the at least one hinge 540 may comprise a first hinge portion 560 connected to an end 432 of the fixed member 430 and a second hinge portion 565 connected to a corresponding connected end 422 of the adjustable member 420. The second hinge portion 565 may be configured to be unlocked from the first hinge portion 560 upon receipt of a pinching force applied by a user to the at least one hinge 540, thereby allowing adjustment of the elevation of the frame 410, as described in greater detail below with reference to FIGS. 20 and 21.

As depicted in FIG. 20, which shows the hinge 540 apart from the fixed member 430 and the adjustable member 420, the first hinge portion 560 may comprise a housing 570 and a pin assembly 580, where the pin assembly is movable with respect to the housing 570. FIG. 21 shows the hinge 540 with the housing 570 of the first hinge portion 560 removed, for purposes of explanation of the operation of the hinge.

With reference to FIG. 21, the pin assembly 580 may include a main pin 582 that extends between an actuating portion 584 and a connecting portion 586 of the pin assembly. The second hinge portion 565 may in turn comprise a socket extension 520 defining a main through hole 522 and a plurality of locking holes 524. The socket extension 520 may be configured to fit in a receiving slot 572 defined by the housing 570, as shown in FIG. 20. The receiving slot 572 of the housing 570 of the first hinge portion 560 may, in turn, be formed by receiving extensions 574, 576 of the housing 570.

The actuating portion 584 of the pin assembly 580 may be disposed on an opposite side of the socket extension 520 and the receiving extensions 574, 576 with respect to the connecting portion 586, such that the main pin 582 slideably extends through the main through hole 522 of the socket extension 520 and corresponding receiving holes 575, 577 of the receiving extensions 574, 576. Furthermore, with reference to FIG. 21, a locking pin 588 may extend from the connecting portion 586 towards the socket extension 520 of the second hinge portion 565 and may be configured to be received by each of the locking holes 524. In the depicted embodiment, for example, four locking holes 524 are provided, and the locking pin 588 is received by the first locking hole.

The pin assembly 580 may be configured to cooperate with a spring 590 to maintain the first and second hinge portions 560, 565 in a locked state, in which the locking pin 588 is engaged with one of the locking holes 524. In this regard, the spring 590 may be disposed around the main pin 582 between a surface of the socket extension 520 and the actuating portion 584, such that, in an unactuated state of the hinge 540, the connecting portion 586 of the pin assembly 580 is biased toward the socket extension 520, and the locking pin 588 is engaged with one of the locking holes 524, as shown in FIG. 21. As such, in the unactuated state shown in FIG. 21, the first hinge portion 560 and the second hinge portion 565 (FIG. 20) are not movable with respect to each other, and the position of the fixed member 430 with respect to the adjustable member 420 is locked and unchangeable.

To change a position of the first hinge portion 560 with respect to the second hinge portion 565, such as by rotating the first hinge portion 560 about an axis A of the main pin 582, a force F2 may be applied to the actuating portion 584 along the axis A to counteract the biasing force of the spring 590 and move the pin assembly 580 along the axis A such that the connecting portion 586 moves away from the socket extension 520 and the locking pin 588 moves out of engagement with the corresponding locking hole 524. The pinching force F2 may be applied, for example, by a user who places an index finger on the actuation portion 584 and a thumb on the housing 570 on an opposite side of the hinge.

With the locking pin 588 disengaged from the corresponding locking hole 524, the first hinge portion 560 (FIG. 20) may be moved with respect to the second hinge portion so as to adjust an angle of the adjustable member 420 with respect to the fixed member 430, as described above. Once the desired angle is achieved between the adjustable member 420 and the fixed member 430, the force F2 may be discontinued, and the locking pin 588 may, as a result, be moved back toward another corresponding locking hole 524 to lock the first hinge portion 560 in place with respect to the second hinge portion 565 as a result of the force of the spring 590.

Accordingly, the positions of the locking holes 524 may be configured to provide certain predefined angles between the fixed member 430 and the adjustable member 420. In some embodiments, the at least one hinge 540 shown in FIG. 20 may be configured to allow adjustment of the elevation to an angle between approximately 0° (e.g., no elevation) to approximately 20°. In the depicted embodiment of FIG. 21, for example, each hole 588 may represent an incremental increase in the elevation angle, such that the first locking hole 524 (with which the locking pin 588 is engaged in FIG. 21), represents an elevation of approximately 0°; the next adjacent locking hole represents an elevation of 5°; the next adjacent locking hole represents an elevation of 10°; and the last locking hole represents an elevation of 15°. Although four locking holes 524 are shown in FIG. 21, other embodiments may have more or fewer locking holes, so as to provide a greater or smaller range of elevation adjustability. For example, three holes may allow an adjustment of the hinge from 0° to 10°, whereas five holes may allow an adjustment of the hinge from 0° to 20°. Moreover, the spacing of the holes may affect the level adjustability. For example several holes spaced relatively close to each other may provider a finer tune adjustment (e.g., providing increments of 2°, 3°, 4°, or 5° between locked positions), whereas several holes spaced relatively far from each other may provider a courser level of adjustment (e.g., providing increments of 5° to 10° between locked positions). Although in the depicted embodiment of FIGS. 20 and 21 incremental increases or decreases in the elevation can be accomplished, in other embodiments the change in elevation may made in a non-incremental fashion (e.g., continuously to any angle within a range of possible angles, such as approximately 0° to 20°).

Turning again to FIGS. 3, 4, and 12, in some embodiments, the frame 110, 410 may comprise a predefined saddle shape. The saddle shape may, for example, be configured to accommodate a corresponding saddle shape of the base portion of the mitral valve to which the device is to be applied. The general configuration of the device (e.g., nominal size and shape) may be based, in some cases, on cardiac ECHO data analysis of different pathologies. As an example, for a device 100 configured to be installed on the mitral valve, the pathologies considered may be Barlow's disease and ischemic mitral regurgitation. Moreover, in some embodiments, the adjustable member 120, 420 may be configured (e.g., sized and shaped) to be positioned proximate the posterior leaflet 63 (FIG. 2), whereas the fixed member 130, 430 may be configured to be positioned proximate the anterior leaflet 62. In this way, the configuration of the adjustable member 120, 420 (e.g., the overall size of the frame 110, 410 as well as the elevation of the adjustable member with respect to the reference plane passing through the fixed member) may be adequately adjusted and customized to the particular patient's anatomy to provide the appropriate degree of support to the posterior leaflet 63, as the posterior leaflet 63 has been observed in many cases to move and experience prolapse more often the anterior leaflet 62.

Turning now to FIG. 3, the device 100 may further comprise an outer covering 150 surrounding the frame 110, 410. The outer covering 150 may, for example comprise a biocompatible fabric, such as Gore-tex® fabric. In other embodiments, the outer covering 150 may comprise a polymer extrusion, such as silicone. In still other embodiments, the outer covering 150 may comprise multiple layers. For example, the frame 110, 410 may be encased by a silicone extrusion, which is further encased by a layer of polymer material (e.g., extended polytetrafluoroethylene (ePFTE)) or polyester. Moreover, the outer covering 150 may, in some embodiments, be continuous, as illustrated, such that the outer covering 150 completely surrounds and encloses the frame 110, 410. In embodiments in which the surgeon requires access to certain portions of the frame 110, 410, such as via access ports (described below) or adjustment ports, the outer covering 150 may include one or more dry seals that provide such access to internal portion, yet prevent bodily fluids from entering. Moreover, areas of the outer covering 150 that include such dry seals or access points may comprise different materials from other portions of the outer covering, such as by including silicone material in the areas of the dry seals or access points.

In some embodiments, the outer covering 150 may be configured to accommodate the largest possible perimeter of the frame 110. For example, the frame 110, 410 may be configured to be adjustable from a maximum perimeter of approximately 33 mm to a minimum perimeter of approximately 25 mm, e.g., via a locking mechanism that prevents expansion or contraction of the size of the device past a certain threshold, as described above. In this case, the outer covering 150 may be sized to have a maximum perimeter of about 33 mm, such that when the frame is adjusted to a smaller size perimeter, the outer covering may be configured to form one or more accordion-like structures 160 (shown in FIG. 8). In FIG. 8, the accordion-like structures 160 are formed proximate the underlying juncture of the adjustable member 120 with the fixed member 130 (e.g., with excess material bunching up in portions near the juncture); however, in other embodiments, such as the embodiment of FIGS. 12-21, the accordion-like structure 160 may be formed proximate the adjustment space 440 shown in FIG. 12 or near other portions of the frame where adjustments in size may occur.

In addition to allowing a surgeon to effect adjustment of the device 100, such as during a procedure in which the device is installed at the patient's mitral valve, in some embodiments, the device 100 may be configured to allow for real-time adjustments of the device post-operatively in a minimally invasive manner (e.g., without requiring surgery).

Turning to FIG. 10, for example, in some embodiments the ends 122, 124 of the adjustable member 120 may comprise extensions 380, 385 that extend from the ends, through a respective portion of the fixed member 130, and out through an access port 390 of the fixed member and the outer covering 150. The extensions 380, 385 may, in some cases, be separate wires that are connected to or otherwise attached to the ends 122, 124 of the adjustable member 120, whereas in other cases the extensions 380, 385 may be integral to each respective end 122, 124, such as when the ends themselves extend through the fixed member to the access port 390. In such cases, the portions of the adjustable member 120 that form the ends 122, 124 (e.g., proximate the commissures) may have a predefined thickness, such as approximately 2 mm to 4 mm in diameter, and may thin out as they extend through the fixed member 130 and form the extensions 380, 385 to a diameter of, for example approximately 0.3 mm to 1 mm, such as 0.35 mm.

In some embodiments, the extensions 380, 385 may have a length of approximately 80 cm to 100 cm and may thus be threaded through a patient's vasculature to an access point in the patient's neck, such as using a snare inserted from a location outside the body (through the patient's vasculature) to pull the extensions out from the device via the access point and out of the patient's body. The ends of the extensions 380, 385 may then be buried under the patient's skin such that they are accessible to the surgeon post-operatively from outside the body. In this way, the size of the device 100 (e.g., the diameter of the device) may be adjusted post-operatively in a minimally invasive manner via the extensions 380, 385, such as 3 months to 6 months following placement of the device on the mitral valve. This may be necessary, for example, due to changes in the anatomy of the patient's heart, such as remodeling of the ventricle as the heart heals or worsens after installation of the device.

For example, following a procedure in which the device 100 is installed, and after the patient is taken off the heart-lung machine, the function of the patient's heart may be analyzed using echocardiography. If it is determined that the device 100 requires adjustment (e.g., needs to be made smaller) to compensate for changes to the heart so as to improve the closure of the mitral valve, the extensions 380, 385 may be accessed from underneath the patient's skin and a catheter may be inserted into the patient's vasculature over the extensions to the location of the access port 390. The surgeon may then pull on one or both extensions 380, 385, which are in turn connected to the ends 122, 124 of the adjustable member 120, to cinch the diameter of the device (e.g., make the device diameter smaller).

In this regard, the extensions 380, 385 may be configured to move in one direction with respect to the access port 390, such as to only be pulled out of the access port to make the diameter of the device smaller. For example, a surface of the extensions 380, 385 in a portion proximate the access port 390 may comprise burs 392 or other angled protrusions that, although tapered or angled to allow withdrawal from the access portion, resist reentry into the fixed member 130, as shown in FIG. 10A. Once the device has been cinched to the appropriate diameter, the extensions 380, 385 may be secured with respect to the fixed member 130 (such as via burs 392, by twisting the extensions together, or via a separate locking mechanism on the access port 390), separated from the adjustable member 120 (e.g., by applying a force to a predefined area of weakness of the extensions 380 in a region proximate the access port to break off an excess length of the extensions), and removed from the body. In some embodiments, radiopaque markers may be provided on portions of the device 100 (e.g., on parts of the adjustable member, the fixed member, the extensions, etc.) to allow the surgeon to see the position of the device as installed on the mitral valve for making such real-time, remote adjustments. Although features for allowing for real-time adjustments as described above are described in terms of the embodiment of FIG. 4, in some cases one or more of the described features may be incorporated into other embodiments, such as the embodiment of FIG. 12 in a similar fashion.

Turning now to FIG. 11, in some embodiments, a method is provided for treating a mitral valve defect. A device may be provided having a frame comprising an adjustable member and a fixed member, wherein each end of the adjustable member is engaged with a corresponding end of the fixed member to form a closed shape. FIG. 11, Block 200. As described above in detail, at least one end of the adjustable member may be configured to be adjustably received by the corresponding end of the fixed member, such that a perimeter of the closed shape defined by the frame is adjustable. The device may be placed proximate a base portion of the mitral valve to be treated. FIG. 11, Block 210. This may be done via a full or mini-thoracotomy or, in some cases, less invasive surgical procedures may be used.

A perimeter of the closed shape defined by the frame may be adjusted by moving the adjustable member with respect to the fixed member. Block 220. For example, the surgeon may move one or both ends of the adjustable member farther into the corresponding ends of the fixed member to decrease the perimeter of the closed shape (e.g., decrease the overall size of the device). Conversely, the surgeon may withdraw one or both ends of the adjustable member from the corresponding ends of the fixed member to increase the perimeter of the closed shape (e.g., increase the overall size of the device). As described above, adjustment of the perimeter of the closed shape defined by the frame may allow the device to fit the mitral valve being treated so as to improve opening or closure of the mitral valve.

In some embodiments, the frame may comprise at least one hinge proximate adjoining ends of the adjustable member and the fixed member. In such embodiments, the method may further include adjusting an elevation of the frame with respect to a reference plane passing through the fixed end by moving portions of the frame with respect to each other, as described above. In other embodiments, the frame may comprise a malleable material, and the method may further comprise adjusting an elevation of the frame with respect to a reference plane passing through the fixed member by applying pressure to portions of the frame, as noted above.

In other embodiments, as shown in FIG. 22, a method for treating a mitral valve defect is provided that comprises providing a device having a frame comprising an adjustable member and a fixed member (such as a frame configured similarly to the frame 410 of FIG. 12), wherein each connected end of the adjustable member is engaged with a corresponding end of the fixed member, and wherein a distance measured along the adjustable member from one connected end to the other connected end is configured to be adjustable, such that a perimeter of a shape defined by the frame is adjustable, illustrated in block 600. The device may be placed proximate a base portion of the mitral valve to be treated, as shown in block 610, and the device may be adjusted by adjusting the perimeter of the shape defined by the frame so as to allow the device to conform to a shape of the mitral valve being treated for improving opening or closure of the mitral valve, as shown in block 620.

In some cases, adjusting the size of the device may include actuating an adjustment mechanism of the frame, where the adjustment mechanism is configured to engage slotted ends of a cinching member extending through the fixed member and the adjustable member. Actuation of the adjustment mechanism may, in turn, move the cinching member with respect to the fixed member and the adjustable member. Adjusting the size of the device may further include enlarging the size of the device by applying an axial force to the adjustment mechanism while actuating the adjustment mechanism, as described above.

The frame may, in some embodiments, comprise at least one hinge proximate adjoining ends of the adjustable member and the fixed member. In such cases, an elevation of the frame may be adjusted with respect to a reference plane passing through the fixed member by actuating the at least one hinge, as shown in block 630. Actuating the at least one hinge may include applying a pinching force to the at least one hinge, and the hinge(s) may be configured to allow adjustment of the elevation to an angle between approximately 0° to approximately 20°. In other embodiments, including embodiments that do not incorporate hinges as described above, the frame may comprise a malleable material, and the method may further include adjusting an elevation of the frame with respect to a reference plane passing through the fixed member by applying pressure to portions of the frame.

The devices and methods depicted in the figures and described above represent only certain configurations of the device and method for treating a mitral valve. The particular configurations and methods will depend on the patient's anatomy, the condition and location of the target site, the preferences of the practitioner, and other considerations. Moreover, certain features described with respect to one depicted embodiment may be interchanged with or combined with other features described with respect to another depicted embodiments in some cases. For example, a mechanism for adjusting the size of the device (e.g., enlarging or decreasing the perimeter of the frame) described with respect to one embodiment may be combined with a mechanism for adjusting the elevation described with respect to another embodiment, etc. In some cases, one or both of the adjustable member and the fixed member of the frame may be comprised of multiple pieces that are connected to each other and/or portions of the other member. Furthermore, the fixed member in some embodiments may be configured to allow for a certain amount of flexibility, such that adjustments in the size of the adjustable member as described above according to various embodiments may be accommodated, and a more comfortable fit with the mitral valve may be provided.

Accordingly, embodiments of the device described herein and illustrated in the figures provide mechanisms for treating a mitral valve defect by fitting the device to the actual pathology of the valve, rather than attempting to replicate a healthy valve (which the patient does not have). In so doing, the device allows the patient's actual valve to work as well as possible, given the valve's diseased condition.

The actual pathology of the valve is accommodated by providing for multiple dimensions of adjustability of the device, including adjustability of the size (e.g., diameter) of the device as well as adjustability of the elevation or inclination of one portion of the device (e.g., the portion supporting the posterior leaflet) with respect to another portion of the device. By lifting up one of the leaflets to more efficiently coapt with the other leaflet, the need to modify chordae may be reduced or eliminated. In other words, adjustments may be made at the level of the valve. Moreover, embodiments of the device allow for real-time adjustments to be made, such that the surgeon is not limited to fitting the device to the patient's valve at the time of the procedure installing the device, but can also monitor the functioning of the device and any changes to the anatomy of the heart after the device is installed and can make adjustments post-operatively in a minimally invasive manner to ensure the best fit of the device to the valve and the best operation of the patient's existing valve structure.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for treating a mitral valve defect comprising:
a frame comprising a fixed member and an adjustable member, the adjustable member comprising connected ends, each connected end being engaged to a corresponding end of the fixed member, wherein the frame defines a conformable shape, and
an adjustment mechanism configured to be actuated by a user to adjust
a distance measured between the connected ends of the adjustable member, such that a perimeter of the conformable shape defined by the frame is adjustable,
wherein the device is configured to be positioned proximate a base portion of a mitral valve and the device is configured to be adjusted to conform to a shape of the mitral valve being treated so as to improve opening or closure of the mitral valve,
wherein the frame comprises at least one hinge proximate adjoining ends of the adjustable member and the fixed member, wherein the at least one hinge is configured to adjust of an elevation of the frame with respect to a reference plane passing through the fixed member,
wherein the adjustment mechanism comprises a gear having a planar surface and a plurality of teeth extending from the planar surface, the gear being configured to rotate around an axis that is substantially perpendicular to the planar surface and substantially parallel to a direction of extension of the plurality of teeth, the gear further being configured to move between a first axial position and a second axial position along the axis, and wherein the gear is configured to rotate around the axis solely in a first direction when the gear is in the first axial position and is further configured to rotate in the first direction and a second direction, opposite the first direction, when the gear is in the second axial position.

2. The device of claim 1, wherein each of the fixed member and the adjustable member defines a lumen, wherein the frame further comprises a cinching member extending through the respective lumens of the fixed member and the adjustable member, wherein the cinching member is movable with respect to the fixed member and the adjustable member to adjust the perimeter of the conformable shape.

3. The device of claim 2, wherein the adjustable member comprises two free ends that are configured to be moved with respect to each other in response to a corresponding movement of the cinching member.

4. The device of claim 2, wherein the cinching member comprises two slotted ends disposed within the fixed member, and wherein the adjustment mechanism is configured to be actuated by a user to engage the slotted ends of the cinching member and move the slotted ends with respect to each other to adjust a length of the adjustable member.

5. The device of claim 4, wherein the gear is disposed over a spring that biases the gear in the first axial position, and wherein the gear is movable from the first axial position to the second axial position upon compression of the spring.

6. The device of claim 1 further comprising an outer covering surrounding the frame.

7. The device of claim 6, wherein the outer covering comprises at least one of a polymer material or polyester.

8. The device of claim 1, wherein the frame comprises nitinol.

9. The device of claim 1, wherein the at least one hinge comprises a first hinge portion connected to an end of the fixed member and a second hinge portion connected to a corresponding end of the adjustable member, wherein the second hinge portion is configured to be unlocked from the first hinge portion upon receipt of a pinching force applied by a user to the at least one hinge, thereby allowing adjustment of the elevation of the frame.

10. The device of claim 1, wherein the at least one hinge is configured to allow adjustment of the elevation to an angle between approximately 0° and approximately 20°.

11. The device of claim 1, wherein the frame comprises a predefined saddle shape.

12. The device of claim 1, wherein the frame comprises a malleable material.

* * * * *